US006803041B2

(12) United States Patent
Mellencamp

(10) Patent No.: US 6,803,041 B2
(45) Date of Patent: Oct. 12, 2004

(54) EQUINE HERPESVIRUS VACCINE

(75) Inventor: Mark W. Mellencamp, St. Joseph, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 130 days.

(21) Appl. No.: 09/812,720

(22) Filed: Mar. 20, 2001

(65) Prior Publication Data

US 2003/0206924 A1 Nov. 6, 2003

(51) Int. Cl.$^7$ ............... A61K 39/27; A61K 39/295; A61K 39/12; A61K 39/145; A61K 45/08; C12N 13/00; C12N 7/04; C12N 7/06; C12N 7/08

(52) U.S. Cl. ............... 424/229.1; 424/202.1; 424/204.1; 424/205.1; 424/206.1; 424/278.1; 424/280.1; 435/173.3; 435/235.1; 435/236; 435/237; 435/238

(58) Field of Search ............... 424/229.1, 202.1, 424/204.1, 205.1, 206.1, 278.1, 280.1, 201.1, 211.1; 435/173.3, 235.1, 236, 237, 238

(56) References Cited

U.S. PATENT DOCUMENTS

| | | | |
|---|---|---|---|
| 3,920,811 A | * 11/1975 | Lund | 424/88 |
| 4,083,958 A | 4/1978 | Bryans | 424/89 |
| 4,110,433 A | 8/1978 | Purdy, III | 424/89 |
| 4,225,582 A | 9/1980 | Crandell | 424/89 |
| 4,500,513 A | * 2/1985 | Brown et al. | 424/89 |
| 4,509,949 A | 4/1985 | Huang et al. | 586/558 |
| 4,615,697 A | 10/1986 | Robinson | 604/890 |
| 4,758,641 A | 7/1988 | Hsu | 526/208 |
| 5,084,271 A | * 1/1992 | Studdert | 424/89 |
| 5,221,722 A | 6/1993 | Sehm | 526/230.5 |
| 5,292,653 A | * 3/1994 | Kit et al. | 435/235.1 |
| 5,462,734 A | * 10/1995 | Letchworth, III et al. | 424/229.1 |
| 5,470,718 A | 11/1995 | O'Callaghan | 435/69.1 |
| 5,084,271 A | 8/1997 | Studdert | 424/229.1 |
| 5,707,629 A | 1/1998 | O'Callaghan | 424/186.1 |
| 5,795,578 A | * 8/1998 | O'Callaghan | 424/229.1 |
| 5,843,451 A | 12/1998 | Compans et al. | 424/192.1 |
| 5,853,715 A | * 12/1998 | Macek et al. | 424/93.1 |
| 5,922,327 A | 7/1999 | Crabb et al. | 424/229.1 |
| 6,025,181 A | 2/2000 | Onions et al. | 435/235.1 |
| 6,083,511 A | 7/2000 | Onions et al. | 424/229.1 |
| 6,171,592 B1 | 1/2001 | Studdert et al. | 424/186.1 |
| 6,193,983 B1 | 2/2001 | Crabb et al. | 424/229.1 |
| 6,207,166 B1 | 3/2001 | Audonnet et al. | 424/199.1 |
| 6,225,111 B1 | 5/2001 | Cochran et al. | 435/320.1 |
| 6,531,136 B1 | 3/2003 | Studdert et al. | 424/198.1 |
| 6,544,526 B1 | 4/2003 | Crabb et al. | 424/189.1 |

FOREIGN PATENT DOCUMENTS

| | | |
|---|---|---|
| EP | 0532833 A1 | 3/1993 |
| EP | 0978286 A1 | 2/2000 |
| EP | 0 978 286 | * 2/2000 |
| WO | WO 97/22701 | 6/1997 |

OTHER PUBLICATIONS

Matsumura et al. Veterinary Microbiology. 1996; 48: 353–365.*

Ellis et al. JAVMA, 1995; 206 (6): 823–832.*

Zhang et al. Virology. 2000; 468: 482–492.*

Bagust et al., "Studies on Equine Herpesiruses", *Australian Veterinary Journal*, 46, Sep. 1970 (pp. 421–427).

Baker, "Vaccines for EHV1", *The Veterinary Record*, Jan., 1983 (pp. 110–111).

Becker, "Prophylakitsche Impfung gegen den EHV (Equine Herpesvirus)–Abort", *Tierärzll. Prax.*, 16, 1988, (pp. 61–63).

Belák et al., "Passive Immunization of Foals to Prevent Respiratory Disease Caused by Equine Herpesvirus Type 2", *Zbl. Vet. Med. B, 27*, 1980, (pp. 826–830).

Borgen et al,. "Equine Herpesvirus 1: Biological and Biophysical Comparison of Two Viruses from Different Clinical Entities", *Intervirology, 4*, 1973 (pp. 189–198).

Bumgardner, "Lymphocytes from ponies experimentally infedted with equine herpesvirus 1: Subpopulation dynamics and their response to mitogens", *Am. J. Vet. Res., 43*, Jul., 1982 (pp. 1308–1310).

Burrows et al., "Trials of an inactivated equid herpesvirus 1 vaccine: Challenge with a subtype 1 virus", *The Veterinary Record*, Apr., 1984 (pp. 369–374).

Campbell et al., "Equine herpesvirus type 1 (EHV1)", *Veterinary bulletin, Commonwealth Agricultural Bureaux, 53*, Feb. 1983 (pp. 135–146).

Carbopol®, "The Proven Polymers in Pharmaceuticals", *Pharmaceutical Bulletin 2*, Apr., 1995 (8 pp.).

Coggins, "Viral Respiratory Disease", *Veterinary Clinics of North America: Large Animal Practice, 1*, May, 1979 (pp. 59–72).

Ciognoul et al., "Pathogenicity of Equine Herpesvirus 1 Subtype 2 for Foals and Adult Pony Mares", *Veterinary Microbiology, 9*, 1984, (pp. 533–542).

Colle et al., "Transcriptional Analyses of the Unique Short Segment of EHV–1 Strain Kentucky A", *Virus Genes, 9*, 1995 (pp. 257–268).

(List continued on next page.)

*Primary Examiner*—Shanon Foley
(74) *Attorney, Agent, or Firm*—Foley & Lardner LLP

(57) ABSTRACT

A vaccine for protecting a horse against diseases associated with EHV-1 and/or EHV-4 is provided. The vaccine commonly includes inactivated EHV-1 (e.g., chemically inactivated EHV-1 KyA virus) and an adjuvant. The adjuvant can include a cross-linked olefinically unsaturated carboxylic acid polymer which may have bioadhesive properties. The vaccine may also include antigens against other equine pathogens such as inactivated EHV-4 and inactivated A1 and/or A2 strains of equine influenza virus. Methods for protecting horses against diseases associated with EHV-1 and/or EHV-4 and methods of producing the equine herpesvirus vaccine are also provided.

33 Claims, No Drawings

OTHER PUBLICATIONS

Colle et al., "Equine herpesvirus–1 strain KyA, a candidate vaccine strain, reduces vital titers in mice challenged with a pathogenic strain, RacL", *Virus Research, 43,* Jan. 1996 (pp. 112–124).

Crandell, et al., "Vaccination of Pregnant Ponies Against Equine Rhinopneumonitis", *Am. J. Vet. Res., 41,* Jul. 1980) (pp. 994–996).

Dutta et al., "Immunity and the Level of Neutralization Antibodies in Foals and Mares Vaccinated with a Modified Live–Virus Rhinopneumonitis Vaccine", *Am. J. Vet. Res., 36,* Apr. 1975 (pp. 445–448).

Dutta et al., "Cell Mediated Immunity in Equine Herpesvirus Type I Infection 1. In vitro Lymphocyte Blastogenesis and Serum Neutralization Antibody in Normal Parturient and Aborting Mares", *Can. J. comp. Med., 41,* Oct., 1977 (p. 404–408).

Dutta et al., "Efficacy of Modified Live–Virus, Equine Rhinopneumonitis Vaccine", *Am. J. Vet. Res., 37,* Mar., 1976 (pp. 350–351).

Eaglesome et al., "Equine Herpesvirus 1 infection in Mares Vaccinated with a Live–virus Rhinopneumonitis Vaccine Attenuated in Cell Culture", *Can. vet. J., 20,* May, 1979 (pp. 145–147).

Fitzpatrick et al., "Immunologic relationships between equine herpesvirus type 1 (equine abortion virus) and type 4 (equine rhinopneumonitis virus)", *Australian Veterinary Journal,* Oct., 1984 (pp. 1947–1952).

Gerber et al., "Effect of Age and Pregnancy on the Antibody and Cell–mediated Immune Responses of Horses to Equine Herpesvirus 1", *Can. J. comp. Med. 41,* Oct., 1977 (pp. 471–478).

Gleeson et al., "Responses of Pregnant Mares to Equine Herpesvirus 1 (EHV1)", *Cornell Vet., 70,* 1980 (pp. 391–400).

Hormer et al., "Isolation of Equine Herpesviruses from Horses with Respiratory Disease", *New Zealand Veterinary Journal, 24,* 1976 (pp. 171–176).

Jackson et al., "equine Herpesvirus 1 infection of Horses: Studies on the Experimentally induced Neurology Disease", *American Journal of Veterinary Research, 38,* June, 1977 (pp. 709–719).

Kawakami et al., "Combined Immunizing Effects of Live and Inactivated Equine Herpesvirus 1 in Horses", *Proc. 4th Int. Conf. Equine Infect. Des. Lyn,* 1976 (pp. 75–82).

Kemeny, "Antigenic Relationships of Equine Herpesvirus Strains Demonstrated by the Plaque Reduction and Neutralization Kinetics Tests", *Can. J. comp. Med., 35,* Oct., 1971 (pp. 279–284).

Kemeny et al., "Isolation of Herpesvirus from Equine Leukocytes: Comparison with Equine Rhinopneumonitis Virus", *Can. J. comp. Med., 34,* Jan., 1970 (pp. 59–65).

Kendrick et al., "Immunity to Equine Herpesvirus 1 infection in Foals During the First Year of Life", *Journals of Reproduction & Fertility Ltd., 27,* 1979 (pp. 615–618).

Matsumura et al., "Lack of virulence of the murine fibroblast adapted strain, Kentucky A (KyA), of equine herpesvirus type 1 (EHV–1) in young horses", *Veterinary Microbiology, 48,* 1996, (pp. 354–365).

Matumoto et al., "Serologic Survey of Equine Rhinopneumonitis Virus Infection among Horses in Various Countries", *Arch. Ges. Virusforsch., 15,* 1965 (pp. 609–624).

Mayr et al., "Charakterisierung enies Stutenabortvirus aus Polen and Vergleich mit bakannten Rhinopneumonitisvirus–Stammen des Pferdes", Mar., 1965 (p. 217–230).

Mayr et al., "Zur Differenzierung, Diagnose und Bekämpfung virusbedingter Erkankungen des Pferdes unter bezonderer Berucksinchtigung der heimischen Kraukheiten", *Berliner und Munchener Tierarztliche Wochenschrift,* 1968 (pp. 372–378).

Mitchell, "Vaccines for EHV1 absortion", *The Veterinary Record,* Mar., 1983 (p. 285).

O'Callaghan et al., "Equine Herpesviruses (Herpesviridae)", *Encyclopedia of Virology, Second Edition, 1,* 1999 (pp. 508–515).

Osterrieder et al., "The Equine Herpesvirus 1 Ir6 Protein That Colocalizes with Nuclear Lamins is involved in Nucleocapsid Egrees and Migrates from Cell to Cell independently of Virus Infection", *Journal of Virology,* Dec. 1998 (pp. 9806–9817).

Patel et al., "The Pathogenicity in Mice of Respiratory, Abortion and Paresis Isolates of Equine Herpesvirus–1", *Veterinary Microbiology, 8,* 1983 (pp. 301–305).

Peacock, "Biological Requirements and Control of Equine Rhinopneumonitis Vaccine (Live Virus)", *J.A.V.M.A., 155,* Jul. 1969 (pp. 310–314).

Perdue et al., "Studies of the Molecular Anatomy of the L–M Cell Strain of Equine Herpes Virus Type 1: Proteins of the Nucleocapsid and Intact Virion", *Virology, 59,* 1974 (pp. 201–216).

Purdy et al., "Equine Rhinopneumonitis Vaccine: Immunogenicity and Safety in Foals", *Am. J. Vet. Res., 39,* May, 1978 (pp. 745–752).

Romvary et al., "Isolation and Properties of Equine Rhinopneumonitis Virus", *Acta Veterinania Academiae Scientiarum Hungaricase, Tomus 19, 3,* 1969 (pp. 311–317).

Stear, "Efficicary of Modified Live–Virus" "Equine Rhinopneumonitis Vaccine", *Am. J. Vet. Res., 37,* Mar., 1976 (pp. 349–351).

Studdert, "Vaccines for equine herpesvirus type 1", *The Veterinary Record,* Apr., 1983 (p. 334).

Studdert et al., "Equine Herpesviruses", *Australian Veterinary Journal, 46,* Mar., 1970 (pp. 83–89).

Thomson et al., "Serological Detection of Equid Herpesvirus 1 Infections of the Respiratory Tract", *Equine Veterinary Journal, 8,* 1976 (pp. 58–65).

Thomson et al., "Experimental Immunization Against Respiratory Disease Due to Equid Herpesvirus 1 Infection (Rhinopneumonitis) using Formalin–Inactivated Virus with Various Adjuvants", *Veterinary Microbiology, 4,* 1979 (pp. 209–222).

van Woensel et al., "A mouse model for testing the pathogenicity of equine herpes virus–1 strains", *Journal of Virological Methods, 54,* 1995 (pp. 39–49).

Wilks et al., "Immunity to Equine Herpesvirus Type 1 (Rhinopneumonitis): In Vitro Lymphocyte Response", *American Journal of Veterinary Research, 37,* May, 1976 (pp. 487–492).

Zhang et al., "Protective immunity against equine herpesvirus type–1 (EHV–1) infection in mice induced by recombinant EHV–1 gD", *Virus Research, 56,* 1998 (pp. 11–24).

ALLEN, G. P.; "Respiratory Infections by Equine Herpesvirus Types 1 and 4"; *Equine Respiratory Diseases;* P. Lekeux (Ed.), Feb. 28, 2002; pp. 1–14; International Veterinary Information Service, Ithaca, New York, USA.

ELLIS, John A., DVM, Ph.D.; BOGDAN; Jaret R.; KANARA, Edward W., DVM; MORLEY, Paul S. DVM; HAINES, Deborah M. DVM, Ph.D.; "Cellular and Antibody Responses to Equine Herpesviruses 1 and 4 Following Vaccination of Horses With Modified–Live and Inactivated Viruses"; *JAVMA;* Mar. 15, 1995; pp. 823–832; vol. 206, No. 6; American Veterinary Medical Association.

Zhang, Yunfei; Smith, Patrick M.; Jennings, Stephen R.; O'Callaghan, Dennis J.; "Quantitation of Virus–Specific Classes of Antibodies Following Immunization of Mice with Attenuated Equine Herpesvirus 1 and Viral Glycoprotein D"; *Virology;* 2000; pp. 482–492; vol. 268; Academic Press.

Turner et al., "Equine Herpes Viruses, 2, Persistence of equine herpesviruses in experimentally infected horses and the experimental induction of abortion," Aust. Vet. J. 1970 Mar; 46(3):90–8.

Studdert, M. J. et al., "Equine Herpesviruses: on the Differentiation of Respiratory from Foetal Strains of Type 1," Aust. Vet. J. Vol. 55, Oct., 1979.

Studdert, M. J. "Restriction Endonuclease DNA Finger printing of Respiratory, Foetal and Perinatal Foal Isolates of Equine Herpesvirus Type 1," Arch. Virol. 77, 249–258 (1983).

\* cited by examiner

EQUINE HERPESVIRUS VACCINE

BACKGROUND

Respiratory diseases are a major cause of economic loss to the equine industry. Equine herpesviruses (EHV), equine influenza viruses (EIV), and the bacterium, *Streptococcus equi* are pathogens most often associated with infectious respiratory disease in horses. World wide, equine herpesviruses are major pathogens associated with morbidity in horses as a result of respiratory infection. Both equine herpesvirus type 1 (EHV-1) and type 4 (EHV-4) can cause respiratory disease. EHV-1 is also associated with abortions and neurological disease. Because of the high degree of mobility and the international nature of the equine industry, efficacious vaccines are needed to reduce the disease and control the spread of these pathogens.

A number of EHV vaccines are available commercially. None, however, generally is capable of conferring long lasting protection and most require frequent booster immunizations to achieve a significant level of protection against EHV infection. The most commonly recommended route of administration is via intramuscular injection, despite the respiratory system being a primary site of the infection in many instances. In addition, some of the commercial vaccines have been reported to cause undesirable side effects. A number of attempts at developing a recombinant vaccine for EHV have been reported. This approach, however, has not yet resulted in the introduction of a commercial recombinant vaccine which has achieved widespread acceptance.

Literature reports have consistently documented a high degree of variability in the capability of vaccines based on EHV-1 strains to provide cross protection against infection by EHV-4 strains. While vaccines based on EHV-4 strains have shown a greater propensity to provide some protection against both EHV-1 and EHV-4 strains, cross protection based on EHV-4 strains has also been reported to show variability.

There is accordingly a continuing need to develop additional vaccines capable of protecting horses against diseases associated with EHV-1 and/or EHV-4. It would also be advantageous to develop vaccine that is effective against EHV-1 and/or EHV-4 which could be administered via intranasally as well as via parenteral methods (e.g., intramuscularly, subcutaneously or intravenously).

SUMMARY

The present invention relates to immunogenic compositions which include an inactivated form of EHV-1. In particular, the application provides a vaccine for protecting horses against diseases associated with EHV-1 and/or EHV-4. The vaccine includes inactivated EHV-1 (e.g., chemically inactivated EHV-1 KyA virus) and typically also includes an adjuvant. The vaccine may also include other components, such as preservative(s), stabilizer(s) and antigens against other equine pathogens. Typically, the antigens against other equine pathogens are also present in an inactivated form, such as inactivated forms of EHV-4 and inactivated strains of equine influenza virus ("EIV"). For example, the vaccine may be a combination vaccine which includes inactivated forms of A1 and/or A2 strains of equine influenza virus in addition to the inactivated EHV-1. Examples of suitable antigens against EIV include inactivated EIV A1 virus strain A/EQ1/Newmarket/77, inactivated EIV A2 virus strain Newmarket/2/93, and inactivated EIV A2 virus strain Kentucky/95.

The terms "vaccine" and "immunogenic composition" are defined herein in a broad sense to refer to any type of biological agent in an administratable form capable of stimulating an immune response in an animal inoculated with the vaccine. For purposes of this invention, the vaccine (immunogenic composition) typically includes the viral agent in an inactivated form. Vaccines in general may be based on either the virus itself or an immunogenic (antigenic) component of the virus. Herein, the term "protection" when used in reference to a vaccine refers to the amelioration (either partial or complete) of any of the symptoms associated with the disease or condition in question. Thus, protection of horses from EHV by the present vaccines generally results in a diminishing of virus shedding and/or one or more of the clinical symptoms associated with infection by EHV-1 and/or EHV-4 (e.g., pyrexia, nasal discharge, conjunctivitis, coughing, dyspnea, depression, and antibiotic treatment required for secondary bacterial infection).

In one embodiment, the present immunogenic compositions include a chemically inactivated form of EHV-1. Vaccines which include chemically inactivated EHV-1 KyA virus are particularly desirable. A variety of chemical inactivating agents known to those skilled in the art may be employed to inactivate the virus. Ethylenimine and related derivatives, such as binary ethylenimine ("BEI") and acetylethylenimine, are examples of suitable chemical inactivating agents for use in inactivating the EHV-1 virus. Other chemical inactivating agents, e.g., beta-propiolactone or aldehydes (such as formaldehyde and glutaraldehyde), can also be used to inactivate the virus.

The present vaccines generally include an adjuvant which desirably may have bioadhesive properties, particularly where the virus is designed to be capable of intranasal administration. Examples of suitable adjuvants include cross-linked olefinically unsaturated carboxylic acid polymers, such as cross-linked acrylic acid polymers. As used herein the term "cross-linked acrylic acid polymer" refers to polymer and copolymers formed from a monomer mixture which includes acrylic acid as the preodominant monomer in the mixture. Examples of suitable cross-linked acrylic acid polymers include those commercially available under the tradenames Carbopol® 934P and Carbopol® 971 (available from B. F. Goodrich Co., Cleveland, Ohio). One particularly suitable adjuvant for use in the present vaccines is a cross-linked acrylic acid polymer having a Brookfield viscosity of no more than about 20,000 cPs (as measured at 20 rpm as a 1.0 wt. % aqueous solution at pH 7.5). Where a bioadhesive adjuvant is desired, it may be advantageous to utilize an adjuvant which has a bioadhesive property of at least about 50 dynes/cm2 as measured between two pieces of freshly excised rabbit stomach tissue (as determined by the procedure described in U.S. Pat. No. 4,615,697).

Methods for protecting horses against diseases associated with EHV-1 and/or EHV-4 which include administering a vaccine containing inactivated EHV-1 to the horses. The vaccine can be administered using a variety of methods including intranasal and/or parenteral (e.g., intramuscular) administration. In one embodiment of the method, the inactivated EHV-1 containing vaccine is first administered intramuscularly one or more times (e.g., at intervals of 2–4 weeks), followed by administration of the vaccine at least once intranasally (e.g., 2–4 weeks after the last parenteral administration of vaccine). The vaccine is advisedly administered to horses that are 6 months or older. Ideally, all horses in a given herd are vaccinated annually in order to protect against the spread of respiratory symptoms of the disease.

A method of producing an equine herpesvirus vaccine is also provided. The method typically includes inoculating simian cells with EHV-1 virus, e.g., with EHV-1 KyA virus. The inoculated simian cells are incubated, generally at least until CPE is observed (commonly after 24 to 120 hours at 36° C.), and then the EHV-1 virus is harvested from the incubated cells (e.g., by decanting and filtering the culture fluids). The harvested virus-containing fluids can be treated with a chemical inactivating agent, such as binary ethylenimine, to form inactivated EHV-1 virus. Typically, the inactivated virus is further processed, e.g., by concentration and blending with other components, to produce a commercial formulation. For example, the fluids containing the inactivated virus may be concentrated and blended with an adjuvant and/or antigen(s) to one or more other equine pathogens.

The present application is also directed to a kit which includes in combination, (1) a dispenser capable of administering a vaccine to a horse; and (2) a chemically inactivated EHV-1 containing vaccine capable of protecting against diseases associated with EHV-1 and/or EHV-4. The kit may include a dispenser which is capable of dispensing its contents as droplets, e.g., as aerosol, atomized spray and/or liquid droplets, and a form of the vaccine which is capable of protecting against diseases associated with EHV-1 and/or EHV-4 when administered at least in part intranasally.

Throughout this application, the text refers to various embodiments of the present compositions and/or related methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

DETAILED DESCRIPTION

The present immunogenic compositions include an inactivated form of EHV-1. The vaccines are designed for protecting horses against diseases associated with EHV-1 and/or EHV-4. The vaccines typically include a chemically inactivated form of EHV-1 and those which include chemically inactivated EHV-1 KyA virus are particularly desirable. A variety of chemical inactivating agents known to those skilled in the art may be employed to inactivate the virus. Ethylenimine and related derivatives, such as binary ethylenimine ("BEI") and acetylethylenimine, are examples of suitable chemical inactivating agents for use in inactivating the EHV-1 virus. Other chemical inactivating agents, e.g., beta-propiolactone, aldehydes (such as formaldehyde) and/or detergents (e.g., Tween® detergent, Triton® X, or alkyl trimethylammonium salts) can also be used to inactivate the virus. The inactivation can be performed using standard methods known to those of skill in the art. Samples can be taken at periodic time intervals and assayed for residual live virus. Monitoring of cytopathic effect on an appropriate cell line and/or fluorescent staining with an appropriate specific monoclonal antibody can be used to detected the presence of residual live virus.

Inactivation with BEI can be accomplished by combining a stock BEI solution (e.g., a solution formed by adding 0.1–0.2 M 2-bromo-ethylamine hydrobromide to 0.1–0.2 N aqueous NaOH) with viral fluids to a final concentration of about 1–2 mM BEI. Inactivation is commonly performed by holding the BEI-virus mixture at 35–40° C. (e.g., 37° C.) with constant mixing for 36–72 hours. Virus inactivation can be halted by the addition of sodium thiosulfate solution to a final concentration in excess of the BEI concentration (e.g., 2–3 mM sodium thiosulfate with 1–2 mM BEI solutions) followed by mixing for several hours.

The present immunogenic compositions usually include an adjuvant and, if desired, one or more emulsifiers such as Tween® detergent incorporated with the inactivated EHV-1. Suitable adjuvants include, for example, vitamin E acetate solubilisate, aluminium hydroxide, aluminium phosphate or aluminium oxide, (mineral) oil emulsions, non-ionic detergents, squalene and saponins. Other adjuvants which may be used include an oil based adjuvants such as Freund's complete adjuvant (FCA), and Freund's incomplete adjuvant (FIA). It has been found that cross-linked olefinically unsaturated carboxylic acid polymers, such as Carbopol® 971 polymer, are particularly suitable adjuvants for use in the present inactivated EHV-1 immunogenic compositions.

One example of such an adjuvant is an olefinically unsaturated carboxylic acid polymer produced by reaction of a monomer mixture which includes one or more olefinically unsaturated carboxylic acid monomers (such as acrylic acid and/or methacrylic acid) and a cross-linking agent. Typically, at least about 90 wt. % of the monomer mixture is olefinically unsaturated carboxylic monomer. The resulting polymer product desirably contains no more than about 0.5 wt. % and, preferably, no more than about 0.2 wt. % unreacted olefinically unsaturated carboxylic monomer. The polymerization reaction can be carried out by reaction of the monomer mixture in the presence of solvent which includes aliphatic ketone, alkyl ester or a mixture thereof. Suitable aliphatic ketones include those having 3 to 6 carbon atoms, such as acetone and cyclohexanone (as used herein the term "aliphatic ketone" includes cycloaliphatic ketones). Examples of suitable alkyl esters include those having 3 to 6 carbon atoms, such as ethyl acetate, ethyl formate, isopropyl acetate, n-propyl acetate, butyl acetate or a mixture thereof.

Suitable olefinically unsaturated carboxylic acid polymer adjuvants desirably have a Brookfield viscosity of no more than about 40,000 cPs (at 20 rpm as a 0.5 wt. % aqueous solution at pH 7.5). Particularly suitable examples include olefinically unsaturated carboxylic acid polymers with a viscosity of no more than about 15,000 cPs and more desirably about 4,000–11,000 cPs (at 20 rpm as a 0.5 wt. % aqueous solution at pH 7.5).

One example of a suitable adjuvant includes a cross-linked acrylic acid polymer formed from a monomer mixture which includes acrylic acid and a cross-linking agent. The cross-linking agent may include a polyalkenyl polyether cross-linking agent, such as a divinyl glycol. Examples of suitable divinyl alcohols include allyl sucrose, allyl pentaerythritol, polyalkylene diol diallyl ether having a molecular weight of no more than 1000, trimethylolpropane diallyl ether, and mixtures thereof. Examples of other useful cross-linking agents are divinylbenzene, N,N-diallylacrylamide, 3,4-dihydroxy-1,5-hexadiene, 2,5-dimethyl-1,5-hexadiene and the like.

Where the vaccine is to be administered intranasally, it may be advantageous to use an adjuvant is bioadhesive with respect to mucous membranes. Bioadhesive polymers generally have the property of being able to adhere to a mucous membrane in the eyes, nose, mouth, gastrointestinal tract, vaginal cavity and rectal canal. Bioadhesive may be broadly defined as a material that adheres to a live or freshly killed biological surface such as mucus membrane or skin tissue. Bioadhesion as that phrase is used herein to define a useful bioadhesive is assayed by a procedure that measures the force required to separate two layers of freshly excised rabbit stomach tissue that are adhered together by an adhesive. Using this procedure, a bioadhesive may be defined as a material that requires a force of at least about 50 dynes/cm.sup.2 to separate two adhered, freshly excised pieces of rabbit stomach tissue, following the procedure described in U.S. Pat. No. 4,615,697, the disclosure of which is herein incorporated by reference. The upper limits for forces required to separate the freshly excised rabbit tissue are not precisely known, but are believed to be at least about 2000 dynes/cm$^2$.

Suitable examples of adjuvants include cross-linked olefinically unsaturated carboxylic acid polymers with bioadhesive properties (e.g., Carbopol® 971 polymer, a cross-linked acrylic acid polymer available from B. F. Goodrich Co., Cleveland, Ohio). Polyacrylic acids of this type are generally crosslinked carboxy-functional polymers that contain specified amounts of carboxyl functionality and crosslinking agent. Such polymers can be a bioadhesive such that the polymers exhibit an adhesion between two pieces of freshly excised rabbit stomach tissue of at least 50 dynes/cm.sup.2 (when measured in the manner described in U.S. Pat. No. 4,615,697).

It is generally advantageous to formulate the present compositions in dosage unit form for ease of administration and uniformity of dosage. Dosage unit form as used herein refers to physically discrete units suited as unitary dosages for the mammalian subjects to the treated; each unit containing a predetermined quantity of the active material calculated to produce the desired therapeutic effect in association with the required pharmaceutical carrier. The specification for the dosage unit forms of inactivated EHV-1 (as well as inactivated EHV-4 and/or inactivated EIV) are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form.

The principal active ingredient is typically compounded for convenient and effective administration in effective amounts with a suitable pharmaceutically acceptable carrier in dosage unit form as disclosed herein. A unit dosage form can, for example, contain the EHV-1 antigen in amounts ranging from 1 to about 5 relative potency units ("RPUs"). This amount of the antigen is generally present in from about 1 to about 25/ml of carrier. In the case of compositions containing supplementary active ingredients (e.g., inactivated EIV and/or inactivated EHV-4), the dosages are determined by reference to the usual dose and manner of administration of the supplementary active ingredients.

The present vaccines typically include inactivated EHV-1 formulated with a pharmaceutically acceptable carrier. The pharmaceutical forms suitable for injectable use commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum, monostearate and gelatin.

Sterile injectable solutions may be prepared by incorporating the inactivated virus in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from a previously sterile-filtered solution thereof.

It may also be advantageous to add a stabilizer to the present compositions to improve the stability of inactivated virus. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

The compositions and methods of the present invention may be illustrated by the following examples, which are presented to illustrate the present invention and to assist in teaching one of ordinary skill how to make and use the same. These examples are not intended in any way to narrow or otherwise limit the scope of the present invention.

EXAMPLE 1

Production of the Fluids Containing Inactivated EHV-1 Strain

To produce the Equine Rhinopneumonitis Vaccine, killed virus, a master seed culture of an EHV-1 was first produced. From this master seed, a culture of EHV-1 was grown and then inactivated. The inactivated virus culture was then mixed with an adjuvant in order to produce the Equine Rhinopneumonitis Vaccine. The following method was used to produce the Equine Rhinopneumonitis Vaccine.

In order to produce the EHV-1 master seed virus culture ("EHV-1 MSV"), equine herpesvirus type 1 strain KyA (EHV-1 KyA) was passaged four times on Vero A139 cells and four times on EVero cells. The fourth passage was used as a master seed virus designated EHV-1 KyA, MSV Lot 001-dil.

From the master seed virus, a culture of EHV-1 was produced by infecting EVero cells with EHV-1 MSV in a minimum essential medium ("MEM") having 0 to 5% serum. Gentamicin was added to the culture medium in an amount sufficient to inhibit bacterial growth. The EVero cells were typically infected with the EHV-1 MSV with a target multiplicity of infection ("MOI") of 0.001. Such cultures can be grown in glass roller bottles or on microcarrier beads. The culture was incubated at 36° C.±2° C. for 24 to 120 hours until cytopathic effect ("CPE") was observed. During incubation, the culture was monitored for EHV induced CPE to ensure a pure EHV strain. If a typical CPE was observed or any macroscopic or microscopic evidence of contamination existed, the culture was discarded. Pure virus culture was aseptically harvested into sterile glass carboys, sterile plastic carboys, or sterile stainless steel tanks and was clarified by filtration through filters of 8 microns or greater. Bulk virus harvest fluids were tested to ensure the absence of mycoplasma prior to inactivation. Harvested fluids which were not immediately inactivated were stored at −40° C. or below.

After being harvested, the virus culture was inactivated in order to produce a killed vaccine. To inactivate the virus, the culture temperature was brought to 36° C.±2° C. Next, a 0.2M solution of 2-bromoethyleneamine hydrobromide was cyclized to binary ethylenimine ("BEI") in 0.15M NaOH and added to the culture to give a final concentration of 2 mM BEI. The resulting mixture was stirred continuously for 48 hours at 36° C.±2° C.

After treatment with BEI, the culture was tested for its ability to induce CPE typical of EHV to ensure inactivation of the virus using the procedure described in Example 3. This task was accomplished by passing the BEI treated viral fluids over EVero cells and checking the EVero cells for any viral infection. The BEI treated culture fluids were typically stored at 2–7° C. or below until the inactivation assay had been completed. After a satisfactory inactivation test showing no viral infection, excess BEI was neutralized by adding a sufficient amount of a cold (4° C.±2° C.) solution of 1.0M sodium thiosulfate to give a final concentration of 6 mM.

Following the inactivation and testing of the EHV-1 culture, the inactivated culture was concentrated, if necessary, by ultrafiltration to a concentration that would allow formulation as a vaccine with a relative potency ("RP") for EHV-1 of at least 1.0 as determined by the EHV potency release assay described in Example 6 herein.

The inactivated virus was formulated as an adjuvanted vaccine by thoroughly blending the inactivated EHV-1 culture with saline and a 0.5% stock solution of the adjuvant Carbopol® 971 to form a bulk serial. A typical 60 L serial was made by blending 3.5–4.0 L inactivated EHV-1 culture fluid, 12 L Carbopol® 971 stock solution and 44–44.5 L saline. The bulk serial was maintained at 2–8° C. until being transferred into vials containing either one or ten doses (@2.2 ml per dose). Each dose of the inactivated vaccine contained at least 1.0 RP value of inactivated EHV-1, 2 mg Carbopol® 971 and a residual amount of gentamicin.

EXAMPLE 2
Production of the Fluids Containing Inactivated Equine Influenza Virus
Equine Influenza Virus—A/EQ1/Newmarket/77, Subtype A1

The MSV Rec ER1K subtype A1 of equine influenza was developed at the Wellcome Foundation Ltd., Beckenham, Kent, U.K. The original equine strain was passaged ten times, alone or in combination with A/Puerto Rico/8/34 virus, in specific pathogen free (SPF) embryonated eggs. Reassortant ER1K was passaged an additional seven times in Vero tissue culture to produce MSV designated A/E/Newmarket/77 (Equi) (H7N7) Rec ER1K. The virus was received by Boehringer Ingelheim Vetmedica, Inc. (BIVI) from Coopers Animal Health, Inc., Est. Lic. No. 107. The virus was passed one time in the EVero cell line [Vero cell line received from Coopers Animal Health has been designated as EVero at BIVI] at BIVI to establish the new master seed virus. The master seed virus is designated as Lot 111795.

Equine Influenza Virus—Newmarket/2/93, Subtype A2

The Newmarket/2/93 subtype A2 of equine influenza was obtained from Dr. J. A. Mummford at the Animal Health Trust, P.O. Box 5 Newmarket, Suffolk CB8 8JH, England. The virus was isolated from a horse with rhinitis. The virus was passaged five times in specific pathogen free (SPF) embryonated chicken eggs and then passaged five times in the Madin-Darby canine kidney (MDCK) cell line. The fifth passage in MDCK cells was designated as MSV. The MSV is designated as EIV NM/2/93, MSV Lot 001-dil.

Equine Influenza—Kentucky/95, Subtype A2

The Kentucky/95 subtype A2 of equine influenza was obtained from the Gluck Equine Research Center, Lexington, Ky. The virus was isolated from a horse with rhinitis. The virus was passaged two times in specific pathogen free (SPF) embryonated chicken eggs. The virus was then passaged three times in Madin-Darby canine kidney (MDCK) cell line and three times in EVero cells. The third passage in EVero cells was designated as MSV. The MSV is designated as EIV K95, MSV Lot 001-dil.

The following procedures were used to produce the three strains of equine influenza components separately, but by similar methods. Each production lot of Newmarket/77 virus was identified as equine influenza virus (EIV) by observing characteristic EIV induced cytopathic effects (CPE) in EVero cells. Each production lot of Newmarket/2/93 and Kentucky/95 virus was identified as EIV by observing characteristic EIV induced CPE in MDCK cells. The Newmarket/77 and Kentucky/95 are cytocidal for monkey kidney cell cultures and produced typical EIV CPE in monolayer cultures. The Newmarket/2/93 is cytocidal for MDCK cell cultures and produced typical EIV CPE in monolayer cultures. Virulence in horses was not evaluated for any of the viruses. The master seed viruses were tested for purity in accordance with 9 C.F.R. 113.27 (c), 113.28, and 113.55. The Newmarket/77 master seed virus was for Swine Vesicular Disease, Akabane, Bovine Ephemeral Fever, Bluetongue, and Velogenic Visceotrophic Newcastle disease. Bulk virus harvest fluids are tested for mycoplasma prior to inactivation in accordance with the 9 C.F.R. 113.28. The master seed viruses were tested for immunogenicity using the following procedure.

Bulk or final container samples of completed product from each serial were tested for potency by a guinea pig potency test. Each of at least ten guinea pigs, weighing 300–500 grams, was injected intramuscularly. Each guinea pig dose was one half of the dose recommended as a unit dose of the vaccine on the label for a horse. A second dose was injected 14 to 21 days after the first dose. Two additional guinea pigs from the same source were held as controls. Fourteen to 21 days after the second injection, serum samples from each vaccinate and each control were tested for Newmarket/77, Newmarket/2/93 and Kentucky/95 antibodies by hemagglutination inhibition (HAI). The potency of the EIV fractions in the vaccine were determined using the National Veterinary Services Laboratories Testing Protocol, Supplemental Assay Method for Conducting the Hemagglutination Inhibition Assay for Equine Influenza Antibody (MVSAM0124.01, dated Oct. 2, 1998).

If the controls did not remain seronegative at 1:10 for the EIV fraction under test, the test was considered a no test and was repeated. If eight of the ten vaccinates in a valid test did not develop HAI antibody titer of 80 or greater for the Newmarket/77 fraction and a titer of 40 or greater for the Newmarket/2/93 and Kentucky/95 fractions, the sample was considered unsatisfactory. Vaccines containing inactivated EIV are desirably formulated to include at least about 64 HAU/unit dose of inactivated EIV virus subtype A1 and/or at least about 256 HAU/unit dose of inactivated EIV virus subtype A2

The first passage through the fourth passage from master seed virus were utilized for working and production seed. Vaccine was produced from the first passage through the fifth passage from master seed virus. Equine Influenza, strain Newmarket/77, subtype A1 and Equine Influenza, strain Kentucky/95, subtype A2 were propagated in EVero Cell Line Cultures.

The MDCK cell line used for propagation of Newmarket/2/93 was confined between passages 71 and 91. Passage 71 was frozen and was designated as the Master Cell Stock. The MDCK cell cultures were propagated in MEM containing 5–10% fetal bovine serum. Seed and production culture of Newmarket/2/93 were propagated in MEM supplemented with 10 units of trypsin/mL. Cell cultures are grown on microcarrier beads in 1, 3, 10, 30, 50, or 140 liter cell culture vessels, 9 L glass roller bottles, or plastic roller bottles. Master and working seed viruses are stored at −60° C. or below.

MDCK cells cultures were grown in sterile glass or plastic containers. The cultures were grown in 75 $cm^2$ or 150 $cm^2$ plastic flasks with 40 to 100 mL of media. Expansion cultures were grown in roller bottle cultures in 100–1000 mL media and then subcultured in roller bottle cultures also. Either a 75 $cm^2$ or 150 $cm^2$ surface attachment area was chosen, based upon the attachment and growth of the cell line when first coming out of the liquid nitrogen repository. Due to the stress of liquid nitrogen storage, in some instances it was advantageous to start cell growth in a smaller surface area, and when growth had been achieved, subculture the cells further into a 150 $cm^2$ T-flask. If the cells came out of liquid nitrogen storage and produced a healthy monolayer of cells sufficient for expansion in a 150 $cm^2$ T-flask, then the 75 $cm^2$ T-flask step was omitted and the cells were planted directly into the 150 $cm^2$ T-flask.

Prior to inoculation with virus, the cell growth medium was decanted from the culture vessel. Minimum essential medium (MEM) without serum was added to the culture vessel and the cells were rinsed for 30 to 45 minutes. The volume of rinse medium was dependent on the culture vessel being used. The culture vessel was inoculated by decanting rinse medium and adding MEM without serum containing 10 Units of purified trypsin/ml MEM and to which seed virus has been added. Cell cultures were infected with a target multiplicity of infection (MOI) of 0.01 for the Newmarket/77, Newmarket/2/93 and Kentucky/95 strains.

The cell cultures were maintained at 36° C.±2° C. until the fluid was harvested. Monolayers were observed following inoculation for characteristic EIV induced changes in cell morphology. CPE included rounding and refractile cells that detached from the monolayer surface. CPE was usually apparent 24–96 hours after inoculation. The culture was examined throughout the incubation period for macroscopic and/or microscopic evidence of contamination or for a typical changes in cell morphology. Any culture exhibiting evidence of microbial contamination or nonspecific cellular degeneration was discarded.

Prior to harvesting, each culture was examined macroscopically and microscopically. Any culture exhibiting evidence of contamination or a typical CPE was discarded. The fluid from the culture vessel(s) was harvested one to four days after inoculation. The virus culture fluid in the culture vessel was aseptically harvested into sterile glass or plastic carboys or a sterile stainless steel tank after clarification by filtration through filters of 8 microns or greater. Pooled fluids were either inactivated immediately or stored at −40° C. or below for inactivation at a later time. Samples were collected for sterility and antigen testing after inactivation.

The volume of culture fluids was determined and the temperature of the fluids was brought to 36° C.±2° C. A 0.2M solution of 2-bromoethyleneamine hydrobromide which had been cyclized to binary ethylenimine (BEI) in 0.15M NaOH was added to the culture fluids to give a final BEI concentration of 2 mM. The inactivated virus fluid was stored either frozen at $\leq$−40° C. or at 4–8° C. until completion of inactivation testing.

Each lot of Newmarket/77 and Kentucky/95 was tested for inactivation by passage in Vero A139 cells. Each lot of Newmarket/2/93 was tested for inactivation by passage in MDCK cells. Appropriate cell culture monolayer (150 ml) was inoculated with 1.0 ml of inactivated EIV fluids and maintained at 36° C.±2° C. for 14 days with at least two passages. At the end of the maintenance period, the cell monolayers were examined for CPE typical of EIV. For positive virus controls, one culture flask each of EVero cells was inoculated with reference Newmarket/77 and Kentucky/95 virus, respectively, and one culture of MDCK cells was inoculated with a reference Newmarket/2/93 virus (each to a target MOI of 0.01). One flask of EVero cells and one flask of MDCK cells remained uninoculated as negative controls. After incubation and passage, the absence of virus-infected cells in the BEI treated viral fluids constituted a satisfactory test for inactivation. The control cells inoculated with the reference virus showed CPE typical of EIV and the uninoculated flask showed no evidence of EIV CPE.

After a satisfactory inactivation test, residual BEI was neutralized by the addition of a cold (4° C.±2° C.) solution of 1.0 M sodium thiosulfate to give a final concentration of 6 mM. The inactivated fluids were stored at 4° C.±2° C. or below until bulking of the final product. If the inactivation test was unsatisfactory, the fluids could be retreated with BEI using the procedure described above and retested for inactivation.

If necessary, each lot of inactivated bulk virus fluid was concentrated 2× to 50× by ultrafiltration to achieve the desired concentration. One or more bulk lots of inactivated bulk virus fluids were usually pooled for concentration. The concentrated bulk virus was held at 4–8° C. until bulking.

The resulting product after inactivation and concentration contained gentamicin in residual amounts from the medium used in the production of the virus harvest fluids. These levels did not exceed the level allowed per dose of product. The vaccine was formulated to contains 2 mg of Carbopol® 971 per dose of vaccine.

The components for bulking were aseptically added to a glass, plastic, or stainless steel container by siphoning, or by positive pressure (sterile-filtered nitrogen). The serial was blended thoroughly and then maintained at 2–8° C. until ready for filling into final containers. The following provides an illustrative inactivated EIV vaccine composition:

| | |
|---|---|
| Newmarket/77 | 3,000 ml |
| Newmarket/2/93 | 6,000 ml |
| Kentucky/95 | 6,000 ml |
| Carbopol® 971 (0.5% stock solution) | 12,000 ml |
| Saline | 33,000 ml |

If desired, the saline or a portion thereof can be substituted by a solution that contains inactivated EHV-1 and, optionally, inactivated EHV-4 to produce a combination EHV/EIV vaccine.

After bulking, the serial was drawn off into sterile plastic or stainless steel containers for transfer to a sterile fill area for filling into final containers, or the bulk serial was sampled and drawn off into sterile plastic carboys. If the serial was drawn off into carboys, it was stored at 4–8° C. If two or more carboys of bulk vaccine were to be filled at a single time, the product was pooled into a sterile stainless steel vessel when required for filling. Each dose of vaccine was formulated to contain sufficient inactivated virus harvest fluids to provide at least 64 hemagglutination units (HAU) of Newmarket/77 and 128 HAU of Newmarket/2/93 and 128 HAU of Kentucky/95.

EXAMPLE 3

Method of Monitoring Inactivation of Viruses

Each lot of EHV-1, EHV-4, EIV Newmarket/77, and EIV Kentucky/95 was tested for inactivation by passage in EVero cells. Each lot of EIV Newmarket/2/93 was tested for inactivation by passage in MDCK cells. One hundred and fifty (150) $cm^2$ of EVero cell culture monolayer were inoculated with 1.0 ml of inactivated EHV or EIV fluids and maintained at 36° C.±2° C. for 14 days with at least two passages. At the end of the maintenance period, the cell monolayers were examined for CPE typical of EHV or EIV. For EHV controls, a culture flask of EVero cells was inoculated with reference EHV-1 or EHV-4 (positive control) to give a target multiplicity (MOI) of 0.001. For EIV controls, a culture flask of EVero cells was inoculated with reference EIV Newmarket/77 or EIV Kentucky/95 virus (positive control) to give a target MOI of 0.01. For the EIV Newmarket/2/93 tests, a culture flask of MDCK cells was inoculated with reference EIV Newmarket/2/93 to give a target MOI of 0.01. As a negative control, a uninoculated flask with EVero cells or MDCK cells was incubated under the same conditions as the test culture(s). After incubation and passage, the absence of virus-infected cells in the BEI treated viral fluids constituted a satisfactory inactivation test. The control cells inoculated with the reference virus should show CPE typical of EHV or EIV. The uninoculated flask should show no evidence of EHV or EIV CPE. After a satisfactory inactivation test, residual BEI was neutralized by the addition of a cold sodium thiosulfate solution and the inactivated fluids were stored at 4° C.±2° C. or below prior to bulk blending of the final product.

EXAMPLE 4

EHV Potency Release Assay

Coating of 96-Well Plates with EHV-1 mAb or EHV-4 mAb 96-well plates used for testing the potency of EHV-1 fractions were coated with the EHV-1 monoclonal antibody. 96-well plates used for testing the potency of EHV-4 containing samples were coated with the EHV-4 monoclonal antibody. The EHV-1 monoclonal antibody ("EHV-1 mAb"), 16H9, IgG fraction, was diluted 1:10,000 in coating buffer. The EHV-4 monoclonal antibody ("EHV-4 mAb"), 20F3, IgG fraction, was diluted 1:10,000 in coating buffer. Aliquots (100 µl) of the mAb solutions were added to all wells of the NUNC MAXISORP plates except the wells in column 1 and the plates were sealed with plate sealing covers. The multiwell plates were then incubated for 1 hour at 37° C. and overnight at 4° C.

Quantification of EHV-1 or EHV-4 Antigen in Test Samples.

EHV-1 or EHV-4 antigens in test samples were quantified using microtiter plates coated with the respective mAb. Prior to testing in the ELISA, one mL aliquots of test samples (e.g., adjuvanted bulk vaccine or final container vaccine) in conical microfuge tubes were frozen at −40° C. or below for a minimum of 18 hours. On the day the ELISA was performed, the frozen sample(s) of test vaccine in microfuge tubes and the frozen vial of the vaccine reference were quickly thawed in a 37° C. water bath and vortexed to resuspend settled material. An aliquot of 2.5 µl Triton® X-100 was added to the microfuge tube of vaccine reference and each microfuge tube of test vaccine. The microfuge tubes were vortexed and incubated at room temperature for one hour. Tubes were votexed every 15 minutes. A 100 µl aliquot of the EHV-1 external reference control (or EHV-4 external reference control) was added to 900 µl of antigen diluent. An aliquot (2.5 µl) Triton® X-100 was added to the diluted EHV-1 external reference. The external reference fluids were incubated at room temperature for 1 hour and vortexed every 15 minutes.

During this one hour incubation, EHV mAb-coated plates were washed three times with PBS-Tween®. Remaining reactive sites in the wells were blocked by post-coating all the wells with 200 µl/well of blocking buffer. Plates were incubated with blocking buffer at 37° C. for a minimum of 30 minutes. After the one hour incubation period, two-fold serial dilutions of the vaccine reference and test vaccine were prepared by transfer of 500 µl of vaccine reference and test sample to a test tube containing 500 µl antigen diluent.

The post-coated plates were washed three times with PBS-Tween® solution. Aliquots (50 µl) from the undiluted through 1:32 dilutions of the reference and test vaccine were added to duplicate wells of EHV-1 mAb and EHV-4 mAb coated plates as shown in Table IV-1. Aliquots of 50 µl of the appropriate external reference control were added to wells of each plate as shown in Table IV-1. Plates were incubated at 37° C. for 1 hour. During this one hour incubation, horse anti-EHV-1 serum (or horse anti-EHV-4 serum) was diluted 1:1,000 in antibody diluent and incubated for one hour at room temperature.

After the one hour incubation, the multiwell plates were washed three times with PBS-Tween® solution. Aliquots (50 µl) of the diluted horse anti-EHV-1 serum (or diluted horse anti-EHV-4 serum) were added to all wells of the appropriate plate except wells in column 1. Plates were then incubated at 37° C. for 1 hour. During this one hour incubation, sheep anti-horse IgG•HRP conjugate was diluted 1:2,500 in antibody diluent and incubated for one hour at room temperature.

After the one hour incubation, plates were again washed three times with PBS-Tween® solution. Aliquots (50 µl) of the sheep anti-horse horse IgG•HRP conjugate were added to all wells of the plate except those in column 1. Plates were incubated at 37° C. for 1 hour. After the one hour incubation, plates were again washed three times with PBS-Tween® solution.

TMB substrate is prepared according to manufacturers instructions. Aliquots (100 µl) of TMB substrate solution were added with a multichannel pipetter to all wells in row A and then in order to rows B through H of the plate. The multiwell plates were then incubated at room temperature. The optical densities of the wells were determined by reading the plate on a microplate reader at a wavelength of 650 nm. The control wells in column 1 served as blanks. Plates used for quantification of EHV-1 antigen were read 35±10 minutes after the addition of TMB substrate. Optical densities in wells containing the EHV-1 external reference should be between 0.500 and 1.200. Plates used for quantification of EHV-4 antigen were read 45±10 minutes after the addition of TMB substrate. Optical densities in wells containing the EHV-4 external reference should be between 0.500 and 1.200. Relative potency values ("RPV") of test vaccine samples were determined from the optical density readings by normalizing values against the EHV-1 external reference control (or EHV-4 external reference control).

III. Criteria for a Valid Test

The optical density in wells containing the EHV-1 external reference (or EHV-4 external reference) should be between 0.500 and 1.200 30±5 minutes after addition of TMB substrate. The optical density in the negative control wells should be no more than 0.250. If either of these validity criteria were not satisfied, the assay should be considered a NO TEST and the assay may be repeated without bias. The relative potency results of an assay were considered satisfactory if RPV (for inactivated EHV-1 and/ or inactivated EHV-4) of a unit dose of the test sample was greater than or equal to 1.0.

IV. Reagents

EHV-1 specific monoclonal antibody, IgG fraction. Hybridoma 16H9 was obtained from Dr. George Allen, Gluck Equine Research Center, University of Kentucky, Lexington, Ky. The IgG fraction from mouse ascites was commercially prepared. The purified antibody was identified as EHV-1 mAb 16H9-IgG, Lot 001, 11-11-98, Exp. 11-11-03. The IgG antibody fraction was stored at 4–8° C.

EHV-4 specific monoclonal antibody, IgG fraction. Hybridoma 20F3 was obtained from Dr. George Allen, Gluck Equine Research Center, University of Kentucky, Lexington, Ky. The IgG fraction from mouse ascites was commercially prepared. The purified antibody was identified as EHV-4 mAb 20F3-IgG, Lot 001/11-11-98, Exp. 11-11-03. The IgG antibody fraction was stored at 4–8° C.

Horse anti-EHV-1 polyclonal serum. A pool of serum was prepared from blood collected from the non-vaccinated control horses in the EHV Immunogenicity Study, 623-510-98E-015, at 21 days post challenge with virulent EHV-1. The antibody was identified as Horse anti-EHV-1, Lot 001/030199, Exp. 030104. The serum was stored frozen at −40° C. or below.

Horse anti-EHV-4 polyclonal serum. A pool of serum was prepared from blood collected from the non-vaccinated control horses in the EHV Immunogenicity Study, 623-510-98E-015, at 21 days post challenge with virulent EHV-4. The antibody was identified as Horse anti-EHV-4, Lot 001/030399, Exp. 030304. The serum was stored frozen at −40° C. or below.

Sheep anti-horse IgG•HRP conjugate, 1 mg/ml, Bethyl Laboratories,Inc. Catolog No. A70-121P. The antibody conjugate was stored at 4–8° C.

EHV-1 external reference fluids. EHV-1 fluids were produced according to the procedure described in Example 1. Vials of EHV-1 external reference fluids were identified as EHV-1 Ext. Ref. Flds., Lot 001/040599. Exp. 040504. Virus fluids were stored at −40° C. or below.

EHV-4 external reference fluids. EHV-4 fluids were produced according to the procedure described in Example 6. Vials of EHV-4 external reference fluids were identified as EHV-4 Ext. Ref. Flds., Lot 001/040699. Exp. 040604. Virus fluids were stored at −40° C. or below.

EHV-1/EHV-4 reference vaccine. The EHV-1/EHV-4 reference vaccine is the same vaccine used in the Immunogenicity study described in Example 8 (623-0510-98E-015). The vaccine was identified as EHV 1 mm. Vac, 623-510-98E-015, lot# 001, 11-6-98. Exp. 110603. The vaccine reference was stored at −40° C. or below.

The following commercially available reagents were used in the experiment:

Substrate system. TMB (two component), Kirkegaard and Perry, catalog no. 50-76-00.

Triton® X-100. Sigma, catalog no. 1043.

Bovine calf serum. Hyclone Laboratories, Inc., catalog no. A-2151-L.

The following standard solutions were prepared for use in the experiment: Coating Buffer (Prepared fresh for each test and adjusted to pH 9.6)

| | g/liter deionized H$_2$O |
|---|---|
| a. Na$_2$CO$_3$.anhydrous | 1.59 |
| b. NaHCO$_3$ | 2.93 |
| PBS (adjusted to pH 7.3) | |
| a. Na$_2$HPO$_4$.anhydrous | 1.18 |
| b. NaH$_2$PO$_4$.anhydrous | 0.23 |
| c. NaCl | 8.50 |
| PBS-Tween ® Solution | |
| a. Na$_2$HPO$_4$.anhydrous | 1.18 |
| b. NaH$_2$PO$_4$.anhydrous | 0.23 |
| c. NaCl | 8.50 |
| d. Tween ® 20 | 0.05 ml |
| Blocking buffer (Prepared fresh on day of test) | |
| a. PBS | 75 ml |
| b. Bovine calf serum | 25 ml |
| Antibody diluent (Aame as blocking buffer; prepared fresh on day of test). | |
| Antigen diluent (Prepared fresh on day of test) | |
| a. PBS | 50 ml |
| b. Triton ® X-100 | 0.05 ml |

EXAMPLE 5

Inoculation of Horses with Inactivated EHV-1 and Subsequent Challenge with Virulent EHV-4

The purpose of the study was to demonstrate immunogenicity of an inactivated EHV-1 KyA virus for cross protection of vaccinated horses challenged with virulent EHV-4. The vaccine used in the study included with inactivated EHV-1 KyA virus adjuvanted with Carbopol® 971. Horses were vaccinated by two different vaccination regimens. One vaccination regimen was three intramuscular vaccinations and the other vaccination regimen was two intramuscular vaccinations and one intranasal administration. Horses were vaccinated at two to four week intervals. Non-vaccinate horses served as controls. At three weeks after the last vaccination, vaccinated and non-vaccinated control horses were challenged with virulent EHV-4.

Severe respiratory disease was observed in non-vaccinated control horses post challenge with EHV-4. Horses vaccinated by either the intramuscular or intramuscular/intranasal regimens with the EHV-1 KyA vaccine showed a significant reduction in clinical signs of respiratory disease caused by EHV-4 compared to non-vaccinated and challenged control horses. There was a significant reduction in virus shedding between horses vaccinated by either vaccination regimen versus non-vaccinated control horses. The results of the study demonstrated the immunogencity of the inactivated EHV-1 KyA fraction of the vaccine against respiratory disease caused by virulent EHV-4. Moreover, the study demonstrated that the inactivated EHV-1 KyA fraction was immunogenic when administered by both the parenteral and parenteral/intranasal routes.

Healthy male and female horses that ranged in age from four to nine months were obtained from selected sources. Horses were identified by halter tag numbers and microchip numbers. All horses were in good health at the start of the study. At the time of the first vaccination, horses had virus neutralization (VN) titers of $\leq 2$ to EHV-1 and EHV-4. Horses were randomized into groups by drawing the identification numbers of the horses from a bag. During the vaccination and challenge periods, horses were maintained together in open pens and were fed free choice dairy quality alfalfa hay, Sweet 14 dietary supplement, equine Biomineral, and water ad libum.

Horses were radomized into groups by drawing horse identification numbers from a bag. Horses were observed for general health and any abnormal behavior during the vaccination period. No abnormal behavior or adverse health conditions were observed in any of the horse post vaccination and no adverse injections site reactions were observed in any horse post vaccination. No clinical signs of respiratory disease were observed in any of the horses during the vaccination period.

EHV-1 fluids for use in the vaccine were produced according to the procedure described in Example 1. All virus fluids were at the fifth passage from master seed virus and were produced on cells at the $20^{th}$ passage from master cell stock. The vaccine was formulated to contain EHV-1 and EIV Newmarket/77, A1 subgroup, EIV Kentucky 95, A2 subgroup and Newmarket 2/93, A2 subgroup, per two ml dose (produced according to the procedure described in Example 2). The vaccine was labeled as EHV-1 Inin Vac, 623-510-99E-116, lot # 001, Dec. 19, 1999.

The immunogenic composition containing inactivated EHV-1 was administered to horses by two vaccination regimens. One vaccination regimen was three intramuscular vaccinations at three week intervals. The other regimen was two intramuscular inoculations at two-four weeks apart followed by a third inoculation by the intranasal route two to four weeks later. Each vaccination regimen group contained 11 or more horses. A group of 18 horses served as non-vaccinated controls. At three weeks after the last vaccination, horses were challenged with virulent EHV-4. Horses were monitored for clinical signs of respiratory disease caused by EHV-4 and the severity of the disease was recorded by a scoring system described below in Table V-1. Blood and nasal samples for serological evaluation and nasal swabs for isolation of virus were taken before and at selected times post vaccination.

TABLE V-1

Clinical Signs Scoring System

| Clinical sign | Score given for each day exhibiting sign |
|---|---|
| Nasal discharge | |
| serous, slight amount | 1 |
| serous copious amount | 2 |
| mucopurulent, slight amount | 3 |
| mucopurulent, copious amount | 4 |

TABLE V-1-continued

Clinical Signs Scoring System

| Clinical sign | Score given for each day exhibiting sign |
|---|---|
| Pyrexia | |
| 102.5–103.9° F. | 1 |
| 104.0–104.9° F. | 2 |
| $\geq$105.0° F. | 3 |
| Other Symptoms | |
| Conjunctivitis | 1 |
| Coughing | 2 |
| Dyspnea | 3 |
| Depression | 4 |
| Antibiotic treatment required for secondary bacterial infection | 5 |

Five replicate titrations of EHV-4 challenge virus, strain 405 were conducted on Vero cells. The titer for the titrations were 4.63 $TCID_{50}$ $Log_{10}$/1 ml for each of the five titrations. Two ml was administered for challenge to give 4.9 $TCID_{50}$ $Log_{10}$/ dose. This dose of virulent virus was sufficient to cause severe clinical respiratory disease in non-vaccinated control horses.

EHV-4 405 strain was obtained from the American Type Culture Collection and was propagated on Vero cells. This virus was isolated from a horse with rhinopneumonitis and was characterized by Dr. M. Studdert, a well recognized scientist in EHV and diseases caused by EHV. The virus was submitted to ATCC as a relevant and representative example of EHV-4 and has previously been recommended by NVSL as an EHV-4 challenge strain.

Frozen stocks of EHV-4 to be used for challenge were thawed and diluted to contain a target concentration of 5.0 $TCID_{50}$ $log_{10}$/ml and frozen at $-70°$ C. A sample of challenge virus was thawed and the titer determined. At the time of challenge, the virus fluids were thawed and two ml of EHV-4 was withdrawn with a three ml syringe and 21 gauge needle. The needle was removed and the challenge virus was administered intranasally to appropriate groups of vaccinated and non-vaccinated horses.

Post challenge, horses were monitored for clinical signs of respiratory disease cause by EHV-4 that included pyrexia, nasal discharge, conjunctivitis, coughing, dyspnea, depression, and other such as antibiotic treatment required for secondary bacterial infection. Horses were observed daily for clinical disease and the severity of disease was recorded.

Nasal swabs for isolation of EHV were taken on selected days post virus challenge and stored at $-70°$ C. Frozen samples were thawed and the swab removed from the transport medium. The sample was processed by centrifugation at 2500×g for 20 minutes at 19–22° C. An aliquot of 0.1 ml of the processed sample was added to a well of a 48-well tissue culture plate containing 24 hour monolayers of Vero cells. Culture plates were incubated at 37° C. in a $CO_2$ incubator for seven days. Wells were observed on a regular basis for the presence of cytopathic effect (CPE) typical of EHV. Wells that exhibited cytotoxicity were subcultured after the seven day incubation period by transfer of 0.2 ml from the well to a well of a 48-well tissue culture plate containing a 24 hour monolayer of Vero cells. Culture plates were incubated at 37° C. in a $CO_2$ incubator for seven days and observed for CPE. The titer of EHV in the processed nasal samples that were positive for CPE was determined by standard titration methods on cells in 96-well tissue culture plates.

Serum VN antibody titers in horses before and after vaccination and after challenge with virulent virus were determined. When blood samples were taken to screen horses for use in the study, all horses had VN antibody titers of $\leq 2$ for EHV-1 and EHV-4, except horse number 13, that had a VN titer of 8 to EHV-1 and EHV-4. At the time of the first vaccination, the VN titer to EHV-1 and EHV-4 had declined to 2 and 4 respectively. One additional horse in the intramuscular group had a VN titer that had increased from 2 to 8 and two horses in the parenteral/intranasal group had VN titers that had increased from 2 to 16. None of the horses showed any evidence of a respiratory infection. Post first vaccination, the increase in VN titer to EHV-1 and EHV-4 was variable but the VN titer in all horses increased relative to the pre-vaccination titer. After the second and third vaccinations, the VN titer remained essentially the same as after post first vaccination. The VN titer was greater to EHV-1 than to EHV-4, although the VN titer to EHV-1 was greater than two-fold but less than four-fold greater than the EHV-4 VN titer. The VN titers to EHV-1 and EHV-4 were greater in the parenteral vaccination group than the parenteral/intranasal group but by less than a two-fold difference. At 21 days post challenge with virulent EHV-4, VN antibody titers to both EHV-1 and EHV-4 had increased slightly or remained the same in the vaccinated horses. However, in non-vaccinated control horses, VN antibody titers increased 32 to 128 fold to both EHV-1 and EHV-4 in all but one non-vaccinated control horses. VN antibody titers to EHV-1 were similar to VN antibody titers to EHV-4 in vaccinated and control horses post EHV4 challenge.

VN antibody titers in nasal samples collected from horses before and after vaccination and after challenge with virulent virus were determined with the same VN assay used to determine antibody titers in serum. Similar to VN activity in serum post vaccination, VN activity in nasal secretions increased after vaccination but to a lesser extent. Post challenge with EHV-4, VN antibody titer increased but only slightly and only in a few horses. VN antibody titer data are not presented in the report.

Horses were challenged intranasally with virulent EHV-4. Post challenge, temperature of horses were taken daily and clinical signs of respiratory disease that included nasal discharge, included conjunctivitis, coughing, dyspnea, and depression were recorded.

Pyrexia in horses post EHV-4 challenge was monitored. Pyrexia was sporadic and of short duration in both vaccinate groups and in the control group. In the majority of horses that exhibited pyrexia, the elevated temperature was observed for only one or two days. One vaccinate horse in the parenteral/intranasal group exhibited pyrexia for four consecutive days. There was no evidence of significant differences in the distribution of pyrexia scores among vaccinate and control groups for days 5 through 8, 10 or 13 post challenge. Statistical analysis was not performed on days 1 through 4, 9, 11, 12, and 14 through 21 because less than two animals had nonzero pyrexia scores. When temperatures were analyzed separately by day using analysis of variance there was evidence of significant reduction of temperature among vaccinate and control groups but only for a few individual days.

Observations of nasal discharge in horses were also made. Nasal discharge was assessed as normal, serous slight amount, serous copious amount, mucopurulent slight amount, and mucopurulent copious amount and scored as 0, 1, 2, 3, and 4 respectively. Three horses in the parenteral vaccinate group exhibited mucopurulent nasal discharge for only one day. All other discharge scores in vaccinate groups were slight of amount of serous discharge that was primarily limited to one o two days. In contrast, non-vaccinated control horses exhibited mucopurulent and serous discharge for multiple consecutive days. There was evidence of significant differences among both vaccinate groups and controls ($\leq 0.0479$) for days 3 through 9 and 11 through 15 post challenge. There was evidence of significant differences in the distribution of nasal discharge scores between the parenteral vaccination group and control group ($p \leq 0.0398$) for days 4, 5, 6, 8, 9, and 11 post challenge and between the parenteral intranasal vaccination and control groups ($p \leq 0.0259$) days 3 through 8 and 11 post challenge.

Post challenge observations of clinical signs of conjuctivitis, coughing, dyspnea, and depression are presented in Table 4. Conjuctivitis was the primary sign observed in vaccinates and was recorded for two to three days. One vaccinate exhibited dyspnea for one day and one vaccinated exhibited coughing for three consecutive days. All other observations of coughing were for one day only. One horse each in the parenteral and parenteral/intranasal vaccinates groups, 8% and 9%, respectively exhibited two signs of clinical disease for only one day. Depression was not observed in any vaccinate. In distinction to vaccinates, 80% of the non-vaccinated control horses exhibited severe clinical signs of disease of coughing and depression for three or more consecutive days post challenge. When clinical signs were analyzed as 0=absent and 1=present, there was evidence of a significant difference in number of animals exhibiting conjuctivitis between the parenteral ($p \leq 0.0313$) and parenteral/intransal ($p \leq 0.0391$) vaccination groups and the non-vaccinated control group for days 3 and 6 through 13 post challenge. There was evidence of a significant difference in reduction of animals exhibiting depression ($p \leq 0.0156$) on day 6 post challenge for both the parenteral and parenteral/intranasal vaccinate groups compared to non-vaccinated controls. There was no evidence of a significant difference between vaccinates and controls for dyspnea.

When number of clinical signs exhibited each day were tallied, there was evidence of significant difference in the distribution of number of clinical signs between parenteral ($p \leq 0.0242$) and parenteral/intranasal ($p \leq 0.0259$) vaccinate groups and non-vaccinated control horses on days 6 through 9 and day 11 post challenge. Clinical sign scores of conjunctivitis, coughing, dyspnea, and depression were scored 1, 2, 3, and 4, respectively as described in Table V-1. A composite clinical scores was calculated by a sum of the nasal discharge and clinical sign scores. Temperatures were not included in the calculation of composite score. The composite clinical score was calculated for each horse for each day post challenge. The total composite clinical score is the sum of the clinical scores for all post challenge days. There was evidence of significant differences in composite clinical score between the parenteral and non-vaccinated control group ($p \leq 0.0331$) on days 3 through 9 and 11 through 15 post challenge and significant differences for total composite score ($p \leq 0.0001$). There was evidence of significant differences in composite clinical score between the parenteral/intranasal and non-vaccinated control group ($p \leq 0.0241$) on days 3 through 9 and 11 through 15 post challenge and significant differences for total composite score ($p \leq 0.0001$).

Virus shedding was monitored in horses after challenge with virulent EHV-4. Nasal samples were collected from horses on days 1 through 7 and every other day until 18 days post challenge. EHV-4 challenge virus was recovered from nasal samples from all but one non-vaccinated control horse. Virus was detected from the majority of non-vaccinated control horses at the $10^{-2}$ dilution. Days 3 through 5 were the major days when virus shedding was detected. Virus was detected from some non-vaccinated control horses on day 6 post challenge but at low levels. Challenge virus was not recovered from vaccinated horses post challenge.

Conclusion

The vaccine containing inactivated EHV-1 KyA virus generated a systemic humoral immune response when administered by both the parenteral and parenteral/intranasal routes. Vaccination of horses with the EHV-1 containing vaccine generated high levels of VN antibody to EHV-1 and to EHV-4. Antibody titers to both EHV-1 and EHV-4 were detected in nasal samples from vaccinated animals but at a relatively low titer. Thus, the inactivated EHV-1 KyA containing vaccine was capable of immunizing horses against EHV-1 and was capable of cross-immunizing horses against EHV-4. No abnormal response to vaccination or reaction site injections were observed in an of the horses post vaccination.

Severe respiratory disease that consisted of prolonged episodes of serous and mucopurulent nasal discharge, conjuctivitis, coughing and depression was observed in non-vaccinated control horses challenged with virulent EHV-4. In contrast, the number of clinical signs of EHV-4 respiratory disease, the severity of the clinical signs and the number of vaccinates exhibiting clinical signs were significantly reduced in vaccinated horses. Horses vaccinated by either the parenteral or parenteral/intranasal routes showed a significant reduction in clinical signs of respiratory disease due to EHV-4 infection. Reduction in clinical disease was supported by data establishing that both parenteral and parenteral/intranasal vaccinated horses did not shed virus post EHV-4 challenge. Nasal samples collected from non-vaccinated control horses contained high levels of virus on multiple days post EHV-4 challenge.

The inactivated EHV-1 KyA antigen contained in the vaccine was immunogenic for cross protection of horses against respiratory disease caused by EHV-4 when administered by the parenteral and parenteral/intranasal routes. In summary, the results of this study demonstrated that a vaccine containing inactivated EHV-1 KyA virus generated VN antibody not only to EHV-1 but cross neutralization antibody to EHV-4. The inactivated EHV-1 KyA containing vaccine was capable of cross protection of horses against respiratory disease caused by virulent EHV-4 when administered using either a parenteral or parenteral/intranasal regime.

EXAMPLE 6

Inoculation of Horses with Inactivated EHV-1 and Subsequent Challenge with Virulent EHV-1

The objective of the study described in this example was to demonstrate the immunogencity of the EHV-1 fraction, when administered by either the intramuscular or intramuscular/intranasal routes, for cross protection of horses against disease caused by virulent EHV-1. An additional objective was to demonstrate non-interference of the EIV fractions present on the immunogenicity of EHV-1.

The purpose of the study was to demonstrate immunogenicity of the EHV-1 fraction of the rhinopneumonitis vaccine, killed virus for protection of vaccinated horses challenged with virulent and EHV-1. The vaccine used in the study was formulated with inactivated EHV-1 and adjuvanted with Carbopol® 971. Horses were vaccinated by two different vaccination regimens. One vaccination regimen was three intramuscular vaccinations and the other vaccination regimen was two intramuscular vaccinations and one intranasal administration. Horses were vaccinated at two to four week intervals. Non-vaccinate horses served as controls. At six weeks after the last vaccination, vaccinated and non-vaccinated control horses were challenged with virulent EHV-1. Clinical signs of severe respiratory disease that included mucopurulent nasal discharge, coughing, dyspnea, and depression were observed in non-vaccinated control horses post challenge with EHV-1.

Horses.

Healthy male and female horses of different breeds, three to four months of age were obtained from several sources. Horses were identified by halter tag numbers and microchip numbers. All horses were in good health at the start of the study with no known previous incidence of respiratory disease caused by EHV. Horses were randomized into groups by drawing the identification numbers of the horses from a bag. During the vaccination and challenge periods, horses were maintained together in open pens and were fed free choice dairy quality alfalfa hay, Sweet 14 dietary supplement, equine Bio-mineral, and water ad libum.

Horses were randomized into groups by drawing horse identification numbers from a bag. Horses were observed for general health and any abnormal behavior during the vaccination period. All horses were in good health at the start of the study. No abnormal behavior or adverse health conditions were observed in any of the horse post vaccination and no adverse injections site reactions were observed in any horse post vaccination. No clinical signs of respiratory disease caused by EHV were observed in any of the horses during the vaccination period.

At approximately three weeks before the intended date of challenge of horses with virulent EHV-1, an outbreak of Strangles occurred in the horses. Samples taken from swollen lymph nodes were submitted to Montana State University diagnostic laboratory and *Streptococcus equi* was isolated from the samples. Penicillin was administered to the horses and horses were vaccinated with a live attenuated *S. equi* vaccine, Pinnacle. Horses were allowed to recover from Strangles for three weeks before challenge with virulent EHV-1. One horse, a non-vaccinated control horse, was removed from the study on the day of challenge with EHV-1. Slight depression and dyspnea were observed and inspiratory squeaks were heard upon examination. Another horse, in the intramuscular vaccinate group, died Sep. 21, 2000, five weeks prior to EHV-1 challenge. The cause of death was pneumonia. A third horse, in the intramuscular vaccinate group, died on Oct. 28, 2000, one day post challenge. The cause of death was a ruptured mesentery abscess and subsequent toxemia. *S. equi* was isolated from the abscess. All horses challenge with EHV-1 were healthy and showed no evidence of *S. equi* infection. All data from the horses removed from the study were not included in the report.

Vaccine.

EHV-1 fluids for use in the vaccine were produced according to the procedure described in Examples 1 and 2. All virus fluids were at the fifth passage from master seed virus and were produced on cells at the $20^{th}$ passage from master cell stock. The vaccine was formulated to contain EHV-1 and EIV Newmarket/77, A1 subgroup, EIV Kentucky 95, A2 subgroup and Newmarket 2/93, A2 subgroup, per two ml dose. The vaccine was labeled as EHV-1 Imm Vac, Lot #001, 6129-0510-00E-045, Aug. 3, 2000.

Study Design.

The vaccine was administered to horses by two vaccination regimens. One vaccination regimen was three intramuscular vaccinations at two to four week intervals. The other regimen was two intramuscular vaccinations at two-four weeks apart and the third vaccination by the intranasal route two to four weeks later. Each vaccination regimen group contained 19–20 horses. A group of 20 horses served as non-vaccinated controls. At six weeks after the last vaccination, horses were challenged with virulent EHV-1. Horses were monitored for clinical signs of respiratory disease caused by EHV-1 and the severity of the disease was recorded. Blood and nasal samples for serological evaluation and nasal swabs for isolation of virus were taken before and at selected times post vaccination. Collection of blood, nasal samples, and nasal swabs are described in the animal study protocol.

Serum VN Antibody Titers to EHV-1 and EHV-4.

Serum VN antibody titers in horses before and after vaccination and challenge with virulent EHV-1 were determined. All horses both the intramuscular and intramuscular/intranasal vaccinate groups had VN antibody titers of $\leq 2$ or 4 to EHV-1 at the time of the first vaccination. One horse in the intramuscular vaccinate group and five horses in the intranasal vaccinate group had VN antibody titers to EHV-4 of 8 or 16 at the time of the first vaccination. VN antibody titers in the non-vaccinated control horses were $\leq 2$ to 16 with the majority at $\leq 2$ or 4 at the time of the first vaccination. None of the horses showed any evidence of a respiratory infection and there was no known previous exposure to EHV. After one vaccination, there was little to no increase in VN titer to EHV-1 and EHV-4. Antibody titers in the non-vaccinated control horses remained unchanged and, in fact, antibody titers in some controls decreased slightly from pre vaccination titers. After the second vaccination, VN antibody titers to EHV-1 increased in the intramuscular and intramuscular/intranasal vaccinate groups. Antibody titers to EHV-4 did not increase in either of the vaccinate groups. Antibody titers in non-vaccinated controls remained unchanged or continued to decline in the non-vaccinated control group. Post third vaccination, the VN titers to EHV-1 continued to increase. Antibody titers to EHV-4 also increased after the third vaccination. The geometric mean VN antibody titers to EHV-1 and EHV-4 in the intramuscular vaccinate group were 86 and 19, respectively and were 69 and 20 for EHV-1 and EHV-4, respectively in the intramuscular/intranasal group. With the exception of three non-vaccinated control horses, antibody titers to EHV-1 and EHV-4 remained unchanged or declined by the end of the third vaccination period. At 21 days post challenge with virulent EHV-1, VN antibody titers to both EHV-1 and EHV-4 increased dramatically in some vaccinates and increased only slightly or remained the same in other vaccinates. However, in non-vaccinated control horses, VN antibody titers increased over 100 fold to both EHV-1 and EHV-4 in all but four non-vaccinated control horses. In general, VN antibody titers were greater to EHV-1 than to EHV-4.

Titration of EHV-1 Challenge Virus.

Five replicate titrations of EHV-1 challenge virus, strain KyD were conducted on Vero cells. Results of the five replicate titrations were 4.4, 4.4, 4.4, 4.4, and 4.5 TCID$_{50}$ Log$_{10}$/ml. The mean titer was 4.4 TCID$_{50}$ Log$_{10}$/ml. Two ml was administered to each horse for challenge to give 4.7 TCID$_{50}$ Log$_{10}$/2 ml dose. The target dose of virus to be administered to horses for challenge was $\geq 4.0$ TCID$_{50}$ Log$_{10}$/2 ml dose.

Challenge of Horses with Virulent EHV-1.

EHV-1 KyD strain was obtained from the American Type Culture Collection and was propagated on Vero cells. Stocks of the EHV-1 to be used for challenge were to contain a target concentration of $\geq 4.0$ TCID$_{50}$ log$_{10}$/ml. Stocks were frozen at $-70°$ C. A sample of challenge virus was thawed and the titer determined. At the time of challenge, the virus fluids were thawed and two ml of the EHV-1 was withdrawn with a three ml syringe and 21 gauge needle. The needle was removed and the challenge virus was administered intranasally to appropriate groups of vaccinated and non-vaccinated horses. Vaccinates and non-vaccinated control horses were housed together in open pens during the 21 day post challenge period.

Post challenge, horses were monitored for pyrexia and clinical signs of respiratory disease cause by EHV-1 that included, nasal discharge, conjunctivitis, coughing, dyspnea, depression, and other such as antibiotic treatment required for secondary bacterial infection. Horses were observed daily for clinical disease and the severity of disease was recorded.

Pyrexia in horses post EHV-1 challenge was monitored. Pyrexia was sporadic and was spread out over the duration of the challenge period. There were horses in the non-vaccinated control group as well as both vaccinate groups that had elevated temperatures for two and three consecutive days but there did not seem to be a correlation of pyrexia with clinical signs of respiratory disease. There was no evidence of significant differences in the distribution of pyrexia scores between each of the vaccinate groups and the non-vaccinated control group.

Observations of nasal discharge in horses were made. Nasal discharge was recorded as normal, serous slight amount, serous copious amount, mucopurulent slight amount, and mucopurulent copious amount and scored as 0, 1, 2, 3, and 4 respectively, according to the animal protocol. Serous nasal discharge was observed post challenge in all horses in the intramuscular vaccinate group with about an equal number of horses exhibiting slight and copious amounts of serous discharge. Horses 405 and 423 had two consecutive days of mucopurulent discharge and horses 420 and 469 had one day of mucopurulent discharge. Non-vaccinated control horses exhibited primarily mucopurulent discharge for multiple consecutive days. When nasal discharge scores are analyzed as per the scoring system in the animal protocol, there is evidence of a significant difference in the distribution of nasal discharge scores between the intramuscular group and non-vaccinated controls group on days 5–7 and 10 post challenge ($p \leq 0.0018$). Similar results of serous nasal discharge were observed in the intramuscular/intranasal group post challenge with mucopurulent discharge recorded for two vaccinates for one or two days. There is evidence of a significant difference in the distribution of nasal discharge scores between the intramuscular/intranasal group and non-vaccinated controls group on days 4–7, 10 and 19 post challenge ($p \leq 0.0463$).

When nasal discharge scores were analyzed according to a system of normal=0, serous=1 and mucopurulent=2, there was evidence of a significant difference between the intramuscular group and non-vaccinated controls group on days 5–7, 10 and 17 post challenge ($p \leq 0.0463$). There was also evidence of a significant difference in the distribution of nasal discharge scores between the intramuscular/intranasal group and non-vaccinated controls group on days 4–7 and 10 post challenge ($p \leq 0.0092$).

Post challenge observations of clinical signs of conjuctivitis, coughing, dyspnea, and depression were also made. Days 3 through 11 post challenge, were days when the most severe signs of disease were observed in horses. Clinical signs of disease occurred most frequently on days 3 through 11 post challenge. There also seemed to be a secondary phase of clinical signs that were observed in vaccinates and controls. However, this was observed in vaccinates for only single days and in controls for multiple days. Coughing and conjuctivitis were the primary signs of clinical disease observed in vaccinates in the intramuscular regimen group. Conjuctivitis and coughing were observed in the vaccinates for no more than three consecutive days. There is evidence of a significant reduction in proportion of animals exhibiting conjuctivitis in the intramuscular group compared to non-vaccinated controls on days 6 and 7 post challenge ($p \leq 0.0197$) and there is evidence of a significant reduction in proportion of animals exhibiting coughing in the intramuscular group compared to non-vaccinated controls on days 4 through 8 post challenge ($p \leq 0.0463$). Conjuctivitis and coughing were the most common clinical signs of disease observed in the intramuscular/intranasal vaccinate group. There is evidence of a significant reduction in proportion of animals exhibiting conjuctivitis in the intramuscular/intranasal group compared to non-vaccinated controls on days 6 and 7 post challenge ($p \leq 0.0197$) and there is evidence of a significant reduction in proportion of animals exhibiting coughing in the intramuscular group compared to non-vaccinated controls on days 5 and 6 post challenge ($p \leq 0.0044$). Depression was not observed in any intramuscular vaccinate post challenge and was observed in only two intramuscular/intranasal vaccinates post challenge. Depression was observed in multiple non-vaccinated control horses for multiple days. In contrast to the vaccinates, non-vaccinated control horses demonstrated multiple signs of disease that in general persisted for four consecutive days and for as long as seven or eight days. Dyspnea was not observed in any vaccinated horse but was observed in two control horses for multiple days. The same two non-vaccinated control horses required antibiotic treatment for secondary bacterial infection. Clinical disease scores, as calculated per the animal protocol are presented in tables 7 and 8 for intramuscular vaccinates versus controls and intramuscular/intranasal vaccinates versus controls, respectively.

The number of clinical signs were tallied for each day and reported as 0, 1, 2, or 3. When number of clinical signs exhibited each day were tallied, there is evidence of significant difference in the distribution of number of clinical signs between intramuscular group and non-vaccinated control group for days 4 through 8 ($p \leq 0.0206$. There is evidence of significant difference in the distribution of number of clinical signs between intramuscular/intrnasal group and non-vaccinated control group for days 5 through 7 ($p \leq 0.0159$).

A composite clinical scores was calculated by a sum of the nasal discharge and clinical sign scores. The Kruskal-Wallis test, a multigroup extension of the two-group Wicoxins's test was used to test the hypothesis of equality of scores among groups. Wilcoxon's test was used to test the hypothesis of reduction in scores for each vaccinate group compared to the control group (a one-sided test) and to test the hypothesis of equality of scores between vaccinate groups (a two-sided test). There is evidence of significant reduction in composite clinical scores between intramuscular group and non-vaccinated control group for days 4 through 7 and day 11 post challenge ($p \leq 0.0372$) and for total composite clinical score ($p \leq 0.0001$). There is evidence of significant reduction in composite clinical scores between intramuscular/intranasal group and non-vaccinated control group for days 4 through 7 and day 11 post challenge ($p \leq 0.0408$) and for total composite clinical score ($p \leq 0.0002$).

A modified composite clinical score, the sum of clinical observation score and nasal discharge score but not pyrexia, was also calculated. There was evidence of significant reduction in modified composite clinical scores between intramuscular group and non-vaccinated control group for days 3 through 8 and days 10, 11 and 19 post challenge ($p \leq 0.0383$) and for total composite clinical score ($p \leq 0.0001$). There was also evidence of significant reduction in composite clinical scores between intramuscular/intranasal group and non-vaccinated control group for days 3 through 7 and days 10, 11 and 19 post challenge ($p \leq 0.0487$) and for total composite clinical score ($p \leq 0.0001$).

Shedding of Virus from Horses Post Challenge.

EHV-1 challenge virus was recovered from nasal samples from all non-vaccinated control horses shed virus post challenge with EHV-1 and stored at $-70°$ C. Frozen samples were thawed and the swab removed from the transport medium. The sample was processed by centrifugation at 2500×g for 20 minutes at $19-22°$ C. An aliquot of 0.1 ml of the processed sample was added to a well of a 48-well tissue culture plate containing 24–48 hour monolayers of Vero cells. Culture plates were incubated at $37°$ C. in a $CO_2$ incubator for seven days. Wells were observed on a regular basis for the presence of cytopathic effect (CPE) typical of EHV. Wells that exhibited cytotoxicity were subcultured after the seven day incubation period by transfer of 0.2 ml from the well to a well of a 48-well tissue culture plate containing a 24 hour monolayer of Vero cells. Culture plates were incubated at $37°$ C. in a $CO_2$ incubator for seven days and observed for CPE. The titer of EHV in the processed nasal samples that were positive for CPE was determined by standard titration methods on cells in 96-well tissue culture plates.

EHV-1 challenge virus was recovered from nasal samples from all non-vaccinated control horses shed virus post challenge with EHV-1. Virus detected in the nasal swabs was identified as EHV-1 by the immunofluorescence assay using EHV-1 specific monoclonal antibody. Virus was detected from non-vaccinated control horses at the $10^{-2}$ to $10^{-3}$ dilutions. Days two through five were the major days when virus shedding was detected. Challenge virus was recovered post challenge from five horses in the intramuscular vaccinate group and from three horses in the intramuscular/intranasal vaccinate group. There is evidence of a significant reduction in proportion of animals exhibiting the presence of virus in intramuscular group compared to non-vaccinated control group for days 2 through 5 ($p \leq 0.0001$) and there is evidence of a significant reduction in proportion of animals exhibiting the presence of virus in intramuscular/intrnasal group compared to non-vaccinated control group for days 2 through 5 ($p \leq 0.0003$).

Criteria for a Satisfactory Study.

The following criteria must be met for a satisfactory EHV immunogenicity study:

Non-vaccinated control horses must remain seronegative to EHV-1 and EHV-4 during the vaccination period and/or not show any clinical sign of disease as an indicator of exposure of test horses to virulent field virus.

Post challenge with virulent EHV-1, there must be a statistically significant reduction in clinical signs of disease in vaccinated animals compared to clinical signs of disease in non-vaccinated control animals.

Conclusions

In this study, groups of male and female foals of three to four months of age were vaccinated with three doses of vaccine administered by either intramuscular or intramuscular/intranasal routes. Following the administration of three doses of vaccine, all vaccinated animals developed VN antibody. Development of the systemic humoral response was similar in animals vaccinated by the intramuscular and intramuscular/intranasal vaccination regimens. Vaccination of horses with the EHV-1 containing vaccine generated high levels of VN antibody to EHV-1 and to EHV-4. Thus, the EHV-1 containing vaccine was capable of immunizing horses against EHV-1 and was capable of cross-immunizing horses against EHV-4. No abnormal response to vaccination or reaction site injections were observed in an of the horses post vaccination.

To evaluate the ability of the EHV-1 containing vaccine to protect horses against respiratory disease caused by EHV-1, clinical signs of respiratory disease in vaccinated horses were compared to clinical disease in non-vaccinated control horses after challenge with a virulent strain of EHV-1 strain KyD. At approximately six weeks post third vaccination with the EHV-1 containing vaccine, vaccinated and non-vaccinated control horses were challenged intranasally with virulent EHV-1. Severe respiratory disease that consisted of prolonged episodes of serous and mucopurulent nasal discharge, conjuctivitis, coughing, depression, and dyspnea were observed in non-vaccinated control horses challenged with virulent EHV-1. In contrast to control animals, the number of clinical signs of EHV-1 respiratory disease, the severity of the clinical signs and the number of vaccinates exhibiting clinical signs were significantly reduced in vaccinated horses. Both the intramuscular and intramuscular/intranasal routes of vaccination were similar in the reduction in clinical signs of respiratory disease due to EHV-1 infection. Reduction in clinical disease in the vaccinates is supported by data that fewer intramuscular and intramuscular/intranasal vaccinated horses shed virus post EHV-1 challenge and shed virus for shorter periods of time.

The results of the study demonstrated that the vaccine containing inactivated EHV-1 generated VN antibody was immunogenic for protection of horses against respiratory disease caused by EHV-1 when administered by either the intramuscular or intramuscular/intranasal routes.

EXAMPLE 7
Production of Immunogenic Compositions Containing Inactivated EHV-1 and EHV-4 Strains To produce the combined vaccine, master seed cultures of EHV-1 and EHV-4es were first produced. From these master seeds, separate cultures of EHV-1 and EHV-4 were grown and then inactivated. The inactivated virus cultures are then mixed with adjuvant to produce the combined vaccine. The method used to produce the combined inactivated EHV-1/EHV-4 vaccine is described below.

Fluids containing inactivated EHV-1 KyA from the master seed virus culture fluid designated EHV-1 KyA, MSV Lot 001-dil were produced according to the procedure described in Example 1.

To create the master seed virus of equine herpesvirus type 4 (EHV-4), personnel from Boehringer Ingelheim Vetmedica, Inc., isolated virus from a horse infected with rhinitis. The isolated virus was passaged five times on Vero A139 cells and three times on EVero cells. The third passage was used as a master seed virus and designated EHV-4, MSV Lot 001-dil.

Cultures of EHV-4 were produced by infecting EVero cells with seed virus contained in a minimum essential medium (MEM) having 0 to 5% serum. The cultures were then incubated at 36° C.±2° C. for 24 to 120 hours in glass roller bottles or on microcarrier beads. During incubation, the cultures were checked for EHV induced cytopathic effects (CPE) to ensure the purity of the EHV strain. If a typical CPE were present or any macroscopic or microscopic evidence of contamination existed, the culture was discarded. Pure virus cultures were aseptically harvested into sterile glass carboys, sterile plastic carboys, or sterile stainless steel tanks and were clarified by filtration through filters of 8 microns or greater. After being harvested, the virus culture was inactivated in order to produce a killed vaccine using the procedure described for EHV-1 in Example 1.

After inactivation, the cultures were tested for CPE typical of EHV to ensure inactivation of the virus using the procedure described in Example 5. This task was accomplished by passing the BEI treated viral fluids over EVero cells and checking the EVero cells for any viral infection. After a satisfactory inactivation test showing no viral infection, the BEI was neutralized by adding a cold (4° C.±2° C.) solution of 1.0 M sodium thiosulfate to give a final concentration of 6 mM.

Following the inactivation and testing of the EHV-1 and EHV-4 cultures, the cultures were blended with an adjuvant to form the final product, the combined inactivated EHV-1/EHV-4 vaccine. This final product contained EHV-1 fluids, EHV-4 fluids, adjuvant stock solution (0.5% Carbopol® 971), and saline solution in a ratio of 3.75:3:00:12.00:41.19. Typically, a batch contained 3,750 mL of EHV-1, 3,000 mL of EHV-4, 12,000 mL of adjuvant solution, and 41,190 mL of saline, yielding a total volume of 60 L of a bulk serial.

EXAMPLE 8
Inoculation of Horses with the Combined EHV-1 and EHV-4 Vaccine and Subsequent Challenge with Virulent EHV-4

An experiment was performed to demonstrate the immunogenicity of the combination inactivated EHV-1/EHV-4 vaccine. Six groups of male and female horses that ranged in age from four to seven months and were virus neutral to EHV-1 and EHV-4 were used in the experiment. As illustrated in the Table VIII-1 below, three groups were challenged with virulent EHV-1 while three groups were challenged with virulent EHV-4. Of the horses challenged with the EHV-1, one group was vaccinated with three intramuscular ("IM") injections, one group was vaccinated with two intramuscular injections followed by one intranasal ("IN") administration, and one group was not vaccinated. Similarly, of the horses challenged with the EHV-4, one group was vaccinated entirely with intramuscular injections, one group was vaccinated with two intramuscular injections followed by one intranasal administration, and one group was not vaccinated.

The horses were vaccinated at three week intervals with 2 ml doses of the combined vaccine having a RPV of 1.0 per dose of inactivated EHV-1 and 1.0 per dose of inactivated EHV-4. During the trial, the horses were monitored for signs of respiratory disease. No clinical signs of respiratory disease were observed in any of the horses during the vaccination period.

TABLE VIII-1

Summary of Combined EHV-1/EHV-4 Vaccine Test

| Group | No. animals | Vaccination Method | Challenge |
|---|---|---|---|
| Group IV-1 | 10 | IM, IM, IM | EHV-1 |
| Group IV-2 | 10 | IM, IM, IN | EHV-1 |
| Group IV-3 | 10 | None (control group) | EHV-1 |
| Group IV-4 | 10 | IM, IM, IM | EHV-4 |
| Group IV-5 | 10 | IM, IM, IN | EHV-4 |
| Group IV-6 | 10 | None (control group) | EHV-4 |

Animals were challenged at 3 weeks after vaccination with either virulent EHV-1 or virulent EHV-4 at a target dose of 5.0 $TCID_{50}$ $Log_{10}/2$ ml. Specifically, EHV-1 Kentucky D strain (approximate dose of 4.5 $TCID_{50}$ $Log_{10}/2$ ml) and EHV-4 405 strain (approximate dose of 4.0 $TCID_{50}$ $Log_{10}/2$ ml) were used as the challenge viruses and were administered intranasally in 2 ml doses (administered as 1 ml dose per nostril). The protection of the vaccine was measured by monitoring the horses for clinical signs of respiratory disease, such as pyrexia, nasal discharge, conjunctivitis, coughing, dyspnea, and depression, and measuring the severity of the disease. Additionally, blood and nasal samples were taken to measure the amount of virus shedding.

Post virus challenge, all groups of vaccinated horses challenged with either EHV-1 or EHV-4 showed a significant reduction in signs of respiratory disease, with little difference displayed between the parenteral vaccinate groups and the parenteral/intranasal vaccinate groups. Specifically, the vaccinated animals experienced a significant decrease in nasal discharge, conjunctivitis, coughing, dyspnea, and depression. These results demonstrate that the EHV-1 and EHV-4 antigens contained in the combined inactivated EHV-1/EHV-4 vaccine are immunogenic when administered by either the parenteral or parenteral/intranasal route.

In addition to the vaccinated horses showing a reduction in respiratory disease, the vaccinated horses also displayed a reduction in virus shedding. Of the vaccinated horses challenged with EHV-1, virus shedding at 1 to 2.5 $log_{10}$ $TCID_{50}$/ml for one to three days was only observed with only 30% of the parenteral vaccinate group and 40% of the parenteral/intranasal group. In contrast, 90% of the non-vaccinated control group shed the virus at 2.5 to 3.75 $log_{10}$ $TCID_{50}$/ml for two to seven days. Similarly, of the vaccinated horses challenged with the virulent EHV-4 strain, virus shedding at 1 to 2.5 $log_{10}$ $TCID_{50}$/ml for one to three days was only observed with 40% of the parenteral vaccinate group and 50% of the parenteral/intranasal group. Again, the non-vaccinated horses exhibited much greater virus shedding with 100% of the non-vaccinated control group shedding the virus at 1 to 5.25 $log_{10}$ $TCID_{50}$/ml for two to seven days. These statistics are evidence of a significant reduction in the amount and number of days the vaccinated horses shed the virus as compared to the non-vaccinated horses. Such evidence establishes that the EHV-1 and EHV-4 antigens contained in the combined inactivated EHV-1/EHV-4 vaccine are immunogenic when administered by either the parenteral or parenteral/intranasal route.

EXAMPLE 9

Inoculation of Horses with the Combined EHV-1/EHV-4/Equine Influenza Vaccine and Subsequent Challenge with Virulent Equine Influenza Virus An experiment was conducted to evaluate the immunogenicity of the EIV vaccine fractions by evaluation of the serological response to the EIV A1 and A2 subgroups in the host animal. The study was also designed to demonstrate noninterference of EIV and EHV components in a combination rhinopneumonitis-influenza vaccine, killed virus by serological evaluation in the host animal. The third objective was to demonstrate that the EIV A1 subgroup and EIV A2 subgroups in the influenza vaccine and the rhinopnuemonitis-influenza combination vaccines are immunogenic when administered by the parenteral and parenteral/intranasal routes.

Study Design.

Vaccine A was administered to horses by two vaccination regimens. One vaccination regimen was three intramuscular vaccinations at three week intervals. The other regimen was two intramuscular vaccinations at three weeks apart and the third vaccination by the intranasal route three weeks later. Each vaccination regimen group contained 20 horses. A group of five horses served as nonvaccinated controls. Blood samples and nasal washings were taken before and at selected times post vaccination for evaluation of the serological response to each of the three EIV vaccine strains. Blood and nasal washings were collected from the horses at periodic intervals. Horses were observed for general health and any abnormal behavior or health conditions during the 63 day experimental period.

Horses.

Healthy male and female horses that ranged in age of seven to nine months were obtained from selected sources. Horses were identified by microchip numbers and were randomized into groups by drawing the identification numbers of the horses from a sack. During the experimental period, horses were maintained in open pens and fed free choice dairy quality alfalfa hay, Sweet 14 dietary supplement, equine Bio-mineral, and water ad libum. Horses were observed for general health and any abnormal behavior during the experimental period. No abnormal behavior or adverse health conditions were observed in any of the horse post vaccination and no adverse injections site reactions were observed in any horse post vaccination. At the time of the first vaccination, horses vaccinated with Vaccine A had hemagglutination inhibition (HAI) antibody titers of $\leq 10$ to EIV A1 and A2 subgroups.

Vaccine.

The vaccine included EIV killed virus that contained EIV subgroup A1 and antigenically relevant EIV A2 subgroup strains. Because, A2 subgroups in North America differ from A2 subgroups in Europe, the vaccine contained strains, designated Kentucky/95 and Newmarket/2/93, that are representative of the A2 subgroups in North America and Europe, respectively. EIV and EHV virus fluids for use in the vaccine were produced according to the procedures described in Example 7. Virus fluids were at the fifth passage from master seed virus and were produced on cells at the $20^{th}$ passage from master cell stock. Vaccine A was formulated to contain 64 HA units of the EIV A1 subgroup, 128 HA units each of the two EIV A2 subgroups, and $\geq 3.0$ relative potency (RP) units of EHV-1 and $\geq 3.0$ relative potency (RP) units of EHV-4 per two ml dose. The vaccine was labeled as EIV/EHV 1 mm/Intfr, 623-0856-98E-107, Vaccine A Lot 001, 12-15-98.

Potency Determination of EIV and EHV Fractions of Vaccine A.

The potency of the EIV fractions in the vaccine were determined by the National Veterinary Services Laboratories Testing Protocol, Supplemental Assay Method for Conducting the Hemagglutination Inhibition Assay for Equine Influenza Antibody (MVSAM0124.01, dated Oct. 2, 1998). Relative potency values of the EHV-1 and EHV-4 fractions in Vaccine A were determine by the EHV ELISA Potency Release Assay described in Example 4. The potency of Vaccine A was satisfactory for the EIV fractions. Ten of ten guinea pigs had HAI antibody titers of 80 or greater for the A1 subgroup and 10 of 10 guinea pigs had HAI antibody titers of 40 or greater for each A2 subgroup in the vaccine. The relative potency value was 4.73 and 3.31 for the EHV-1 and EHV-4 fractions, respectively.

Serum HAI Antibody Titers to EIV Subgroups A1 and A2 Post Vaccination.

The HAI antibody titers in horses after vaccination with Vaccine A were determined. All vaccinates were seronegative to all three EIV strains at the time of the first vaccination. At the prevaccination time period, two of the nonvaccinated control horses had HAI antibody titers of 20 to the EIV A1 and the other three control horses were seronegative to the EIV A1. All five nonvaccinated control horses were seronegative to the two EIV A2. During the experimental period, nonvaccinated control horses remained seronegative to the two EIV subgroup A2 and did not show more than a two-fold variation in HAI antibody titer to the EIV subgroup A1. There was no indication of exposure to field EIV during the experimental period. At three weeks post first vaccination, the majority of horses showed a serological response to the EIV A1 subgroup and to the EIV A2 NM subgroup. After one vaccination, only four horses had a serological response to the EIV A2 K subgroup. The number of horses with a serological response to the EIV A2 K subgroup increased after the second vaccination. After the third vaccination, 19 of 20 horses (95%) that received three intramuscular vaccinations had HAI antibody titers of 40 or greater to the EIV A1 subgroup. After three intramuscular injections, 18 of 20 (90%) and 20 of 20 (100%) of the horses had HAI antibody titers of 20 or greater to the EIV A2 K and EIV A2 NM subgroups, respectively. Similarly, 17 of 20 horses (85%) that received two intramuscular vaccinations and one intranasal vaccination had HAI antibody titers of 40 or greater to the EIV A1 subgroup. Eighteen of 20 (90%) and 20 of 20 (100%) horses had HAI antibody titers of 20 or greater to the EIV A2 K and EIV A2 NM subgroups, respectively, after two intramuscular and one intranasal vaccination. Geometric mean antibody titers after the third vaccination were 45, 35 and 61 for the EIV A1, A2 K, and A2 NM subgroups, respectively, in horses that received three intramuscular injections. Geometric mean antibody titers in horses that received two intramuscular and one intranasal vaccination were 39, 24, and 51 for the EIV A1, A2 K, and A2 NM subgroups, respectively.

Mucosal HAI Antibody Titers to EIV Subgroups A1 and A2 Post Vaccination.

The HAI antibody titers in nasal samples of horses after vaccination with Vaccine A were determined. At the time of the first vaccination, AHI antibody to the two EIV A2 subgroups were not detected in any nasal samples from the horses. Hemagglutination inhibition titers to the EIV subgroup A1 were detected in some of the vaccinates and nonvaccinated control horses at the first vaccination. After the first and second vaccination, levels of AHI antibody in nasal secretions were variable. After the final intramuscular or intranasal vaccination, HAI antibody levels were highest to the EIV A1 subgroup compared to the two A2 subgroups. There was little to no HAI antibody to the EIV A2 K subgroup in nasal samples from horses post third vaccination by either intramuscular or intranasal routs. Interestingly, HAI antibody levels to the EIV A1 subgroup and A2 NM subgroup were lower in horses that received the third vaccination by the intranasal route.

Discussion

One purpose of this study was to demonstrate the immunogenicity of the EIV A1 and A2 fractions in the vaccine, when administered by either vaccination regimen. Immunogenicity was assessed by determination of the serum HAI antibody response to the three EIV strains after the final vaccination. Results demonstrated that greater than 80% of the horses in both vaccination regimen groups had serum HAI antibody titers of 40 or greater to the EIV A1 subgroup after the final vaccination and greater than 80% of the horses in both vaccination regimen groups had serum HAI antibody titers of 20 or greater to both EIV A2 subgroups after the final vaccination. HAI antibody levels to the EIV A1 and A2 subgroups were also determined in nasal samples at selected times post vaccination. Mucosal HAI antibody titers were lower than serum HAI antibody titers in nasal samples from horses in both vaccination regimens and, in contrast to serum HAI titers, mucosal HAI titers increased very little after each vaccination. It is possible that the hemagglutination inhibition assay does not detect the isotype of antibody that is most prevalent in nasal samples. The experiments demonstrates that the EIV A1 subgroup and A2 subgroups in the influenza vaccine, killed virus and the rhinopneumonitis-influenza vaccine, killed virus, were immunogenic when administered by both the parenteral and parenteral/intranasal routes. In particular, the study demonstrated that the EIV NM/77 A1 subgroup and the K95 A2 subgroup and NM/2/93 A2 subgroups were immunogenic.

Another purpose of the study was to demonstrate non-interference of the EIV and EHV vaccine fractions with each other. Vaccine A used in the study was formulated with the minimum release dose of 64 and 128 HA units of the EIV A1 and A2 fractions, respectively, and formulated with a relative potency value of three fold or greater for the EHV-1 and EHV-4 fractions. Results of the study demonstrated that a vaccine containing the minimum antigen dose of the EIV fractions and more than the minimum EHV antigen dose is capable of generating a satisfactory serological response to the EIV A1 and A2 subgroups in the host animal. Thus, the EHV-1 and EHV-4 fractions did not interfere with the immunogenicity of the EIV vaccine fractions. Likewise, the EHV fractions did not result in an unsatisfactory potency test in the guinea pig model.

The invention has been described with reference to various specific and illustrative embodiments and techniques. However, it should be understood that many variations and modifications may be made while remaining within the spirit and scope of the invention. While various embodiments are discussed in some detail herein, it should be appreciated that the present invention provides inventive concepts which can be embodied in a wide variety of specific contexts. The specific embodiments discussed herein are merely illustrative of specific ways to make and use the present immunogenic compositions and are not meant to limit the scope of the invention. Various modifications and combinations of the illustrative embodiments, as well as other embodiments of the invention, will be apparent to persons skilled in the art upon reference to the disclosure herein.

TABLE IV-1

PLATE TEMPLATE FOR EHV ELISA

|   | 1 | 2 | 3 | 4 | 5 | 6 | 7 | 8 | 9 | 10 | 11 | 12 |
|---|---|---|---|---|---|---|---|---|---|---|---|---|
| A |   | Ref Vaccine | Ref Vaccine | Test 1 Vaccine | Test 1 Vaccine | Test 2 Vaccine | Test 2 Vaccine | Test 3 Vaccine | Test 3 Vaccine | Test 4 Vaccine | Test 4 Vaccine |   |
| B | Blank | Undilute | Undilute | Undilute | Undilute | Undilute | Undilute | Undilute | Undilute | Undilute | Undilute | External Reference |
| C | Blank | 1:2 | 1:2 | 1:2 | 1:2 | 1:2 | 1:2 | 1:2 | 1:2 | 1:2 | 1:2 | External Reference |

TABLE IV-1-continued

PLATE TEMPLATE FOR EHV ELISA

| | 1 | 2 | 3 | 4 | 5 | 6 | 7 | 8 | 9 | 10 | 11 | 12 |
|---|---|---|---|---|---|---|---|---|---|---|---|---|
| D | Blank | 1:4 | 1:4 | 1:4 | 1:4 | 1:4 | 1:4 | 1:4 | 1:4 | 1:4 | 1:4 | External Reference |
| E | Blank | 1:8 | 1:8 | 1:8 | 1:8 | 1:8 | 1:8 | 1:8 | 1:8 | 1:8 | 1:8 | Negative Control |
| F | | 1:16 | 1:16 | 1:16 | 1:16 | 1:16 | 1:16 | 1:16 | 1:16 | 1:16 | 1:16 | Negative Control |
| G | | 1:32 | 1:32 | 1:32 | 1:32 | 1:32 | 1:32 | 1:32 | 1:32 | 1:32 | 1:32 | Negative Control |
| H | | | | | | | | | | | | |

What is claimed is:

1. A vaccine for protecting a horse against diseases associated with EHV-1, EHV-4 or a combination thereof comprising:
   chemically inactivated EHV-1 KyA virus; and
   an adjuvant which includes cross-linked olefinically unsaturated carboxylic acid polymer.

2. The vaccine of claim 1 wherein the EHV-1 KyA virus is chemically inactivated by treatment with a chemical inactivating agent which includes a compound selected from the group consisting of ethylenimine, binary ethylenimine, acetylethylenimine and mixtures thereof.

3. The vaccine of claim 2 wherein the EHV-1 KyA virus is chemically inactivated by treatment with binary ethylenimine.

4. The vaccine of claim 1 further comprising inactivated EHV-4.

5. The vaccine of claim 1 further comprising inactivated equine influenza virus.

6. The vaccine of 5 wherein the inactivated equine influenza virus includes inactivated EIV virus subtype A1.

7. The vaccine of 5 wherein the inactivated equine influenza virus includes inactivated EIV virus subtype A2.

8. The vaccine of 5 comprising inactivated EIV virus subtype A1 and inactivated EIV virus subtype A2.

9. The vaccine of claim 1 wherein said vaccine is capable of protecting horses against EHV-1 and EHV-4.

10. The vaccine of claim 1 wherein the cross-linked olefinically unsaturated carboxylic acid polymer includes cross-linked acrylic acid polymer.

11. A vaccine for protecting a horse against diseases associated with EHV-1 EHV-4 or a combination thereof comprising:
   EHV-1 KyA virus inactivated by treatment with a chemical inactivating agent which includes ethylenimine, binary ethylenimine, acetylethylenimine or a mixture thereof; and
   a bioadhesive adjuvant which includes a cross-linked olefinically unsaturated carboxylic acid polymer.

12. The vaccine of claim 11 wherein the chemical inactivating agent includes binary ethylenimine.

13. The vaccine of claim 11 further comprising inactivated EHV-4.

14. The vaccine of claim 11 futher comprising inactivated EIV virus subtype A1 and inactivated EIV virus subtype A2.

15. A vaccine for protecting a horse against diseases associated with EHV-1, EHV-4 or a combination thereof comprising:
   EHV-1 KyA virus inactivated by treatment with a chemical inactivating agent which includes ethylenimine, binary ethylenimine, acetylethyleflimine or a mixture thereof; and.
   a bioadhesive adjuvant which includes a cross-linked acrylic acid polymer.

16. The vaccine of claim 15 further comprising inactivated EHV-4.

17. The vaccine of claim 15 further comprising inactivated equine influenza virus.

18. The vaccine of claim 17 wherein the inactivated equine influenza virus includes inactivated EIV virus subtype A1.

19. The vaccine of claim 17 wherein the inactivated equine influenza virus includes inactivated EIV virus subtype A2.

20. The vaccine of claim 17 comprising inactivated EIV virus subtype A1 and inactivated EIV virus subtype A2.

21. The vaccine of claim 15 further comprising gentamicin.

22. The vaccine of claim 15 comprising EHV-1 KyA virus inactivated by treatment with a chemical inactivating agent which includes binary ethylenimine.

23. The vaccine of claim 15 wherein the cross-linked acrylic acid polymer has a viscosity of no more than about 20,000 cPs at 20 rpm as a 1.0 wt. % aqueous solution at pH 7.5.

24. A method for protecting a horse against diseases associated with EHV-1, EHV-4 or a combination thereof comprising:
   administering to said horse a vaccine comprising chemically inactivated EHV-1 KyA virus and an adjuvant which includes cross-linked olefinically unsaturated carboxylic acid polymer.

25. The method of claim 24 wherein administering the vaccine to said horse comprises:
   parenterally administering the vaccine; and
   intranasally administering the vaccine.

26. The method of claim 25 wherein administering the vaccine to said horse comprises:
   parenterally administering the vaccine at least once in a first step; and
   intranasally administering the vaccine in a subsequent step.

27. The method of claim 24 wherein the vaccine further comprises inactivated EHV-4.

28. The method of claim 24 wherein the vaccine further comprises inactivated equine influenza virus.

29. The method of claim 28 wherein the vaccine comprises inactivated EIV virus subtype A1 and inactivated EIV virus subtype A2.

30. A kit comprising in combination, (1) a dispenser capable of administering a vaccine to a horse; and (2) a composition to protect against diseases associated with EHV-1, EHV-4 or a combination thereof, wherein the composition comprises:

chemically inactivated EHV-1 KyA virus; and
an adjuvant which includes cross-linked olefinically unsaturated carboxylic acid polymer.

31. The kit of claim 30 wherein the dispenser is capable of dispensing its contents as droplets; and the composition is capable of protecting against diseases associated with EHV-1, EHV-4 or a combination thereof when administered intranasally.

32. The kit of claim 30 wherein the chemically inactivated EHV-1 KyA virus is chemically inactivated by treatment with binary ethylenimine.

33. The kit of claim 30 wherein the composition further comprises inactivated EIV virus subtype A1 and inactivated EIV virus subtype A2.

* * * * *

UNITED STATES PATENT AND TRADEMARK OFFICE
CERTIFICATE OF CORRECTION

PATENT NO. : 6,803,041 B2
DATED : October 12, 2004
INVENTOR(S) : Mark W. Mellencamp It is certified that error appears in the above-identified patent and that said Letters Patent is hereby corrected as shown below:

Column 31,
Lines 35, 37 and 39, preceding "5" insert -- claim --.
Line 66, following "ethylenimine," delete "acetylethyleflimine" and substitute -- acetylethylenimine --.

Signed and Sealed this

Eighth Day of February, 2005

JON W. DUDAS
*Director of the United States Patent and Trademark Office*